(12) United States Patent
Twardzik et al.

(10) Patent No.: US 7,329,645 B2
(45) Date of Patent: *Feb. 12, 2008

(54) TGF-α POLYPEPTIDES, FUNCTIONAL FRAGMENTS AND METHODS OF USE THEREFOR

(75) Inventors: Daniel R. Twardzik, Bainbridge Island, WA (US); Andre Pernet, Lake Forest, IL (US); Thomas S. Felker, Vashon, WA (US); Stefan Paskell, Bainbridge Island, WA (US)

(73) Assignee: Applied Protein Sciences, LLC, Mountain View, CA (US)

( * ) Notice: Subject to any disclaimer, the term of this patent is extended or adjusted under 35 U.S.C. 154(b) by 641 days.

This patent is subject to a terminal disclaimer.

(21) Appl. No.: 10/050,190

(22) Filed: Jan. 15, 2002

(65) Prior Publication Data

US 2002/0123465 A1 Sep. 5, 2002

Related U.S. Application Data

(63) Continuation of application No. 09/641,587, filed on Aug. 17, 2000, now abandoned, which is a continuation-in-part of application No. 09/492,935, filed on Jan. 27, 2000, which is a continuation-in-part of application No. 09/378,567, filed on Aug. 19, 1999, now abandoned.

(51) Int. Cl.
  A61K 38/16 (2006.01)
  A61K 38/19 (2006.01)

(52) U.S. Cl. .............................. 514/12; 514/2; 530/300

(58) Field of Classification Search .................. 530/300; 514/2, 12
See application file for complete search history.

(56) References Cited

U.S. PATENT DOCUMENTS

| | | | |
|---|---|---|---|
| 4,742,003 A | 5/1988 | Derynck et al. | |
| 4,749,683 A | 6/1988 | Murphy et al. | |
| 4,863,899 A | 9/1989 | Todaro | |
| 4,863,902 A | 9/1989 | Amagase et al. | |
| 4,874,746 A | 10/1989 | Antoniades et al. | |
| 5,102,870 A | 4/1992 | Florine et al. | |
| 5,229,493 A | 7/1993 | Folkman et al. | |
| 5,240,912 A | 8/1993 | Todaro | |
| 5,328,986 A | 7/1994 | Folkman et al. | |
| 5,690,928 A | 11/1997 | Heimbrook et al. | |
| 5,750,376 A | 5/1998 | Weiss et al. | |
| 5,814,308 A | 9/1998 | Zhang | |
| 5,851,832 A | 12/1998 | Weiss et al. | |
| 5,885,956 A | 3/1999 | Nardi et al. | |
| 5,886,141 A | 3/1999 | Folkman et al. | |
| 5,902,799 A | 5/1999 | Herrmann et al. | |
| 5,942,487 A | 8/1999 | Ogawa et al. | |
| 5,980,885 A | 11/1999 | Weiss et al. | |
| 5,981,165 A | 11/1999 | Weiss et al. | |
| 6,011,004 A | 1/2000 | Kessler et al. | |
| 6,013,762 A | 1/2000 | Folkman et al. | |
| 6,071,889 A | 6/2000 | Weiss et al. | |
| 6,114,307 A | 9/2000 | Jaspers et al. | |
| 6,232,288 B1 | 5/2001 | Kojima | |
| 6,288,301 B1 | 9/2001 | Nardi et al. | |
| 6,326,201 B1 | 12/2001 | Fung et al. | |
| 6,486,122 B1 | 11/2002 | Twardzik et al. | |

FOREIGN PATENT DOCUMENTS

| | | |
|---|---|---|
| EP | 0 154 434 A1 | 9/1985 |
| WO | WO 84/01106 | 3/1984 |
| WO | WO 94/16718 | 8/1994 |
| WO | WO 95/19785 | 7/1995 |
| WO | WO 95/24466 | 9/1995 |
| WO | WO 96/21676 | 7/1996 |
| WO | WO 97/25349 | 7/1997 |
| WO | WO 98/19712 | 5/1998 |
| WO | WO 98/22127 | 5/1998 |
| WO | WO 99/06060 | 2/1999 |
| WO | WO 99/56785 | 11/1999 |
| WO | WO 00/44400 | 8/2000 |
| WO | WO 00/65028 | 11/2000 |
| WO | WO 03/016480 A2 | 2/2003 |

OTHER PUBLICATIONS

Blikslager, Anthony T. et al., "Glutamine and Transforming Growth Factor–α Stimulate Extracellular Regulated Kinases and Enhance Recovery of Villous Surface Area In Porcine Ischemic–Injured Intestine," *Surgery*, vol. 125, No. 2, Feb. 1999, pp. 186–194.

Blikslager, A.T. et al., "Glutamine and Transforming Growth Factor Alpha Enhance Repair of Intestinal Ischemia/Reperfusion Injury," *Supplement to Gastroenterology*, vol. 110, No. 4, Apr. 1996, Abstract p. A313.

Brand, Stephan A. et al., "Prolonged Efficacy of Islet Neogenesis Therapy with Gastrin and TGFα In Mature Rats with Preexisting Diabetes," *Diabetes*, vol. 50 (Supplement), 2001, p. A338.5630.

Burgel, Pierre–Regis et al., "The Human Eosinophils Induce Mucin Production In Airway Epithelial Cells Via Epidermal Growth Factor Receptor Activation," *The Journal of Immunology*, 2001, pp. 5948–5954.

Carpenter, Graham et al., "Antibodies to the Epidermal Growth Factor Receptor Block the Biological Activities of Sarcoma Growth Factor," *Proc. Natl. Acad. Sci. USA*, vol. 80, Sep. 1983, pp. 5627–5631.

(Continued)

*Primary Examiner*—Brenda Brumback
*Assistant Examiner*—Stephen Gucker
(74) *Attorney, Agent, or Firm*—Seed Intellectual Property Law Group PLLC

(57) ABSTRACT

Disclosed are TGF-α polypeptides, related polypeptides, fragments and mimetics thereof useful in stimulating stem cell or precursor cell proliferation, migration and differentiation. The methods of the invention are useful to treat tissue injury as well as expand stem cell populations in, or obtained from, gastrointestinal, musculoskeletal, urogenital, neurological and cardiovascular tissues. The methods include ex vivo and in vivo applications.

10 Claims, 4 Drawing Sheets

OTHER PUBLICATIONS

Chamberlin, Stephen G. et al., "Constrained Peptide Analogues of Transforming Growth Factor–α Residues Cysteine 21–32 Are Mitogenically Active," *The Journal of Biological Chemistry*, vol. 270, No. 36, Sep. 8, 1995, pp. 21062–21067.

Chosidow, O. et al., "Tripe Palms Associated With Systemic Mastocytosis: The Role of Transforming Growth Factor–α and Efficacy of Interferon–Alfa," *British Journal of Dermatology*, vol. 138, 1998, pp. 698–703.

Chou and Fasman, "Prediction of Protein Conformation," *Biochemistry*, vol. 13, No. 2, 1974, pp. 222–245.

Coffey, Robert J. et al., "Transforming Growth Factors and Related Peptides in Gastrointestinal Neoplasia," *Journal of Cellular Biochemistry*, Supplement 16G, 1992, pp. 111–118.

Dayhoff, M.O. et al., "A Model of Evolutionary Change in Proteins," *Atlas of Protein Sequence and Structure*, 1972, pp. 89–99.

De Larco, Joseph E. et al., "Sarcoma Growth Factor from Mouse Sarcoma Virus–Transformed Cells," *The Journal of Biological Chemistry*, vol. 255, No. 8, Apr. 25, 1980, pp. 3685–3690.

Draoui, Muriel et al., "TGFα–PE40 Inhibits Non–Small Cell Lung Cancer Growth," *Life Sciences*, vol. 54, No. 7, 1994, pp. 445–453.

Dunbar and Goddard, "Structure–function and Biological Role of Betacellulin," *The International Journal of Biochemistry & Cell Biology*, vol. 32, 2000, pp. 805–815.

Ebadi, M. et al., "Neurotrophins and Their Receptors In Nerve Injury and Repair," *Neurochem. Int.*, vol. 30, Nos. 4/5, 1997, pp. 347–374.

Egger, B. "Reduced Susceptibility of Mice Overexpressing Transforming Growth Factor α To Dextran Sodium Sulphate Induced Colitis," *Gut*, vol. 43, 1998, pp. 64–70.

Faber–Elman, A. et al., "Involvement of Wound–Associated Factors In Rat Brain Astrocycte Migratory Response to Axonal Injury In Vitro Simulation," *J. Clin. Invest.*, vol. 97, No. 1, Jan. 1996, pp. 162–171.

Ferrar, Isidre et al., "Transforming Growth Factor–α (TGF–α) and Epidermal Growth Factor–Receptor (EGF–R) Immunoreactivity In Normal and Pathologic Brain," *Progress In Neurobiology*, vol. 49, 1996, pp. 99–123.

Ghielli, Manuela et al., "Regeneration Processes In the Kidney After Acute Injury: Role of Infiltrating Cells," *Exp. Nephrol.*, vol. 6, 1998, pp. 502–507.

Hardie, William D. et al., "Dose–Dependent Lung Remodeling In Transgenic Mice Expressing Transforming Growth factor–α, " *Am. J. Physiol. Lung Cell. Mol. Physiol.*, vol. 281, 2001, pp. L1088–L1094.

Hardie, William D. et al., "Attenuation of Acute Lung Injury In Transgenic Mice Expressing Human Transforming Growth factor–α," *Am. J. Physiol.*, vol. 277, 1999, pp. L1045–L1050.

Heidenkummer and Kampik, "Immunohistochemical Localization of Epidermal Growth Factor Receptor In A Human Epiretinal Membrane," *Graefe's Arch. Chn. Exp. Ophthalmol.*, vol. 229, 1991, pp. 492–496.

Ibbotson, K.J. et al., "Tumor–Derived Growth Factor Increases Bone Resorption in A Tumor Associated with Humoral Hypercalcemia of Maignancy," *Science*, vol. 221, pp. 1292–1294 (1992).

Jackowski, Andre, "Neural Injury Repair: Hope For the Future As Barriers to Effective CNS Regeneration Become Clearer," *British Journal of Neurosurgery*, vol. 9, 1995, pp. 303–317.

Jackson, Bruce A. et al., "Effects of transforming Growth Factor β and Interleukin–1β on Expression of Cyclooxygenase 1 and 2 and Phospholipase $A_2$ mRNA In Lung Fibroblasts and Endothelial Cells in Culture," *Biochemical and Biophysical Research Communications*, vol. 197, No. 3, Dec. 30, 1993, pp. 1465–1474.

Jayaraman, Gurunathan et al., "Conformational Studies of a Synthetic Cyclic Decapeptide Fragment of Rat Transforming Growth Factor–α," *Int. J. Peptide Protein Res.*, vol. 46, 1995, pp. 88–96.

Jones, M.K. et al., "Gastrointestinal Mucolsal Regeneration: Role of Growth Factors," *Frontiers in Bioscience*, vol. 4, Mar. 15, 1999, pp. d303–d309.

Kheradmand, Farrah et al., "Transforming Growth Factor–α Enhances Alveolar Epithelial cell Repair In a New In Vitro Model," *Am. J. Physiol.*, vol. 267, 1994, pp. L728–L738.

Kobayashi, Kenzo et al., "The Mechanisms of Gastrointestinal Mucosal Injury and Repair," *Japanese Journal of Clinica*, vol. 56, No. 9, Sep. 15, 1998, pp. 7 (2215)–14 (2222) (English abstract).

Konturek, Peter Ch. et al., "Epidermal Growth Factor and Transforming Growth Factor–α: Role In Protection and Healing of Gastric Mucosal Lesions," *European Journal of Gastroenterology & Hepatology*, vol. 7, 1995, pp. 933–938.

Konturek, S.J. et al., "Transforming Growth Facctor Alpha and Epidermal Growth Factor In Protection and Healing of Gastric Mucosal Injury," *Scand. J. Gastroenterol.*, vol. 27, 1992, pp. 649–655.

Kornblum, Harley I. et al., "Prenatal Ontogeny of the Epidermal Growth Factor Receptor and Its Ligand, Transforming Growth Factor Alpha, in the Rat Brain," *The Journal of Comparative Neurology*, vol. 380, 1997, pp. 243–261.

Kudlow, Jeffrey E. et al., "Inability of Anti–Epidermal Growth Factor Receptor Monoclonal Antibody to Block "Autocrine" Growth Stimulation in Transforming Growth Factor–Secreting Melanoma Cells," *The Journal of Biological Chemistry*, vol. 259, No. 19, Oct. 10, 1984, pp. 11895–11900.

Lefebvre, Ph. P. et al., "Regeneration of the Neurosensory Structures in the Mammalian Inner Ear," *Acta. Oto–rhino–laryngologica belg.*, vol. 51, 1997, pp. 1–10.

Leong, Hoyee et al., "Cytostatic Effects of 3,3'–Diindolylmethane In Human Endometrial Cancer Cells Result from an Estrogen Receptor–Mediated Increase in Transforming Growth Factor–α Expression," *Carcinogenesis*, vol. 22, No. 11, 2001, pp. 1809–1817.

Liu, Dan et al., "TGF–α Can Act as Morphogen and/or Mitogen in a Colon–Cancer Cell Line," *Int. J. Cancer*, vol. 56, 1994, pp. 603–608.

Liu, Mark C. et al., "Allergy, Rhinitis, other Respiratory Diseases: Effects of Prednisone On the Cellular Responses and Release of Cytokines and Mediators After Segmental Allergen Challenge of Asthmatic Subjects," *Journal of Allergy and Clinical Immunology*, vol. 108, No. 1, Jul. 2001, 16 pages.

Liu, Ming et al., "Immunohistochemical Study of Transforming Growth Factor–Alpha in Human Lung Cancers," *Tumor Biol.*, vol. 13, 1992, pp. 294–298.

Lord, Bl. et al., "Kinetics of Neutrophil Production in Normal and Neutropenic Animals During the Response to Filgrastim (r–metHu G–CSF) Filgrastim SD/01 (PEG–r–metHu G–CSF)," *Clin. Cancer Res.*, vol. 7, Jul. 2001, pp. 2085–2001, pp. 2085–2090.

Marquardt and Todaro, "Purification and Primary Structure of a Polypeptide with Multiplication–Stimulating Activity from Rat Liver Cell Cultures," *The Journal of Biological Chemistry*, vol. 256, No. 13, Jul. 10, 1981, pp. 6859–6865.

Marquardt, Hans et al., "Transforming Growth Factors Produced By RetrovirusTransformed Rodent Fibroblasts and Human Melanoma Cells: Amino Acid Sequence Homology with Epidermal Growth Factor," *Proc. Natl. Acad. Sci. USA*, vol. 80, Aug. 1983, pp. 4684–4688.

Miettinen, Paivi J., "Transforming Growth Factor–α and Epidermal Growth Factor Expression in Human Fetal Gastrointestional Tract," *Pediatric Research*, vol. 33, No. 5, 1993, pp. 481–486.

Mogi, Makio et al., "Interleuken–1β, Interleukin–6, Epidermal Growth Factor and Transforming Growth Factor–α are Elevated in the Brain from Parkinsonian Patients," *Neuroscience Letters*, vol. 180, 1994, pp. 147–150.

Nestor, Jr., John J. et al., "A Synthetic Fragment of Rat Transforming Growth Factor α with receptor Binding and Antigenic Properties," *Biochemical and Biophysical Research Communications*, vol. 129, No. 1, May 31, 1985, pp. 226–232.

Ozanne, Brad et al., "Kirsten Murine Sarcoma Virus transformed Cell Lines and a Spontaneously Transformed rat Cell–Line Produce Transforming Factors," *Journal of Cellular Physiology*, vol. 105, 1980, pp. 163–180.

Reid, S. et al., "Radial Migration of Subependymal Cells in the Adult Rodent Forebrain," *Society for Neuroscience*, vol. 22, 1996, p. 1956 (Abstract).

Rimaniol, Anne–Cecile et al., "Biphasic Transforming Growth Factor–β Production Flanking the Pro–Inflammatory Cytokine Response in Cerebral Trauma," *NeuroReport*, vol. 7, 1995, pp. 133–136.

Romano, Marco et al., "Transforming Growth Factor α Protection Against Drug–Induced Injury to the Rat Gastric Mucosa In Vivo," *J. Clin. Invest.*, vol. 90, 1992, pp. 2409–2421.

Rudinger, J., "Characteristics of the Amino Acids as Components of a Peptide Hormone Sequence," *Biological Council: Peptide Hormones*, Jun. 1976, pp. 1–7.

Sagar, S.M. et al., "Rapid Communication: Epidermal Growth Factor and Transforming Growth Factor α Induce c–fos Gene Expression in Retinal Muller Cells In Vivo," *Journal of Neuroscience Research*, vol. 29, 1991, pp. 549–559.

Sasada, Reiko et al., "Cloning and Expression of cDNA Encoding Human Betacellulin, A New Member of the EGF Family," *Biochemical and Biophysical Research Communications*, vol. 190, No. 3, 1993, pp. 1173–1179.

Scheiman, James M. et al., "Transforming Growth Factor–Alpha (TGFα) Levels in Human Proximal Gastrointestinal Epithelium: Effects of Mucosal Injury and Acid Inhibition," *Digestive Diseases and Sciences*, vol. 42, No. 2, Feb. 1997, pp. 333–341.

Schultz and Twardzik, "Assessment of Biological Activity of Synthetic Fragments of Transforming Growth Factor α," *Methods In Enzymology*, vol. 198, 1991, pp. 200–213.

Shing, Y. et al., "Betacellulin: A Mitogen from Pancreatic β Cell Tumors," *Science*, vol. 259, Mar. 12, 1992, pp. 1604–1607.

Skolnick and Fetrow, "From Genes to protein Structure and Function: Novel Application of Computational Approaches in the Genomic Era," *TIBTECH*, vol. 18, Jan. 2000, pp. 34–38.

Song, Si young et al., "Expansion of Pdx1–Expressing Pancreatic Epithelium and Islet Neogenesis in Transgenic Mice Overexpressing Transforming Growth Factor α," *Gastroenterology*, vol. 117, 1999, pp. 1416–1426.

Sottili, Mauro et al., "Up–Regulation of Transforming Growth Factor αBinding Sites in Experimental Rabbit Colitis," *Gastroenterology*, vol. 109, 1995, pp. 24–31.

Sporn and Todaro, "Autocrine Secretion and Malignant Transformation of Cells," *The New England Journal of Medicine*, vol. 303, No. 15, Oct. 9, 1980, pp. 878–880.

Subauste and Proud, "Effects of Tumor Necrosis Factor–α, Epidermal Growth Factor and Transforming Growth Factor–α on Interleukin–8 Production By, and Human Rhinovirus Replication in , Bronchial Epithelial Cells," *International Immunopharmacology*, vol. 1, 2001, pp. 1229–1234.

Todaro, George J. et al., "Transforming Growth Factors (TGFs): Properties and Possible Mechanisms of Action," *Journal of Supramolecular Structure and Cellular Biochemistry*, vol. 15, 1981, pp. 287–301.

Twardzik, Daniel R. et al., "Similar Transforming Growth Factors (TGFs) Produced by Cells Transformed by Different Isolates of Feline Sarcoma Virus," *Virology*, vol. 124, 1983, pp. 201–207.

Weickert and Blum, "Striatal TGF–α: Postnatal Developmental Expression and Evidence for a Role in the Proliferation of Subependymal Cells," *Developmental Brain Research*, vol. 86, 1995, pp. 203–216.

Yamamoto, Koji et al., "Recombinant Human Betacellulin Promotes the Neogenesis of α–Cells and Ameliorates Glucose Intolerance in Mice With Diabetes Induced by Selective Alloxan Perfusion," *Diabetes*, vol. 49, Dec. 2000, pp. 2021–2027.

Yang, Xiao–Dong et al., "Development of ABX–EGF, A Fully Human Anti–EGF Receptor Monoclonal Antibody, for Cancer Therapy," *Critical Reviews in Oncology/Hematology*, vol. 38, 2001, pp. 17–23.

Zhang, Maobin et al., "Transforming Growth Factor α and a PC 12–Derived Growth Factor Induce Neurites in PC12 Cells and Enhance the Survival of Embryonic Brain Neurons," *Cell Regulation*, vol. 1, Jun. 1990, pp. 511–521.

Cashman, Johanne D. et al., "Mechanisms That Regulate the Cell Cycle Status of Very Primitive Hematopoietic Cells in Long–Term Human Marrow Cultures. I. Stimulatory Role of a Variety of Mesenchymal Cell Activators and Inhibitory Role of TGF–α", *Blood*, vol. 75, No. 1, pp. 96–101, 1990.

Gandrillon, Olivier et al., "TFG–α cooperates with TFG–α to induce the self–renewal of normal erthrocytic progenitors: evidence for an autocrine mechanism", *European Molecular Biology Organization*, vol. 18, No. 10, pp. 2764–2781, 1999.

Hayman, Michael J. et al., "Self–Renewal and Differentiation of Normal Avian Erythroid Progenitor Cells: Regulatory Roles of the TGFα/c–ErbB and SCF/c–Kit Receptors", *Cell*, vol. 74, pp. 157–169, 1993.

Huang, Frederick S. et al., "Role of epidermal growth factor and its receptor in chemotherapy–induced intestinal injury", *Am. J. Physiol. Gastrointest Liver Physiol.* vol. 282, pp. G432–G442, 2002.

Justicia, Carles and Planas, Anna M., "Transforming Growth Factor–α Acting at the Epidermal Growth Factor Receptor Reduces Infarct Volume After Permanent Middle Cerebral Artery Occulsion in Rats", *Journal of Cerebral Blood Flow and Metabolism*, vol. 19, pp. 128–132, 1999.

Rudinger, J., "Characteristics of the amino acids as components of a peptide hormone sequence", Biological Council, The Co-ordinating Committee for Symposia on Drug Action, pp. 1–7, 1976 (out of print).

Sharp, Richard et al., "Transforming growth factor α disrupts the normal program of cellular differentiationi nthe gastric mucosa of transgenic mice", *Development*, vol. 121, pp. 149–161, 1995.

Walz, Thomas M., "Transforming Growth Factor–α (TGF–α) in Human Bone Marrow: Demonstration of TFG–α in Erythroblasts and Eosinophilic Precursor Cells and of Epidermal Growth Factor Receptors in Blastlike Cells of Myelomonocytic Origin", *Blood*, vol. 85, No. 9, pp. 2385–2392, 1995.

Yamashita, Hiroshi and Oesterle, Elizabeth, "Induction of cell proliferation in mammalian inner–ear sensory epithelia by transforming growth factor α and epidermal growth factor", *Proc. Natl. Acad. Sci. USA*, vol. 92, pp. 3152–3155.

Nestor et al., "A Synthetic Fragment of Rat Transforming Growth Factor α With Receptor Binding and Antigenic Properties," *Biochemical and Biophysical Research Communications* 129(1):226–232 (1985).

TGFα

```
                            SEQUENCE LISTING

<160> NUMBER OF SEQ ID NOS: 7

<210> SEQ ID NO 1
<211> LENGTH: 50
<212> TYPE: PRT
<213> ORGANISM: Homo sapiens

<400> SEQUENCE: 1

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
                20                  25                  30

Val Cys His Ser Gly Tyr Val Gly Ala Arg Cys Glu His Ala Asp Leu
            35                  40                  45

Leu Ala
    50

<210> SEQ ID NO 2
<211> LENGTH: 50
<212> TYPE: PRT
<213> ORGANISM: Rattus norvegicus

<400> SEQUENCE: 2

Val Val Ser His Phe Asn Lys Cys Pro Asp Ser His Thr Gln Tyr Cys
1               5                   10                  15
```

-continued

```
Phe His Gly Thr Cys Arg Phe Leu Val Gln Glu Glu Lys Pro Ala Cys
            20                  25                  30

Val Cys His Ser Gly Tyr Val Gly Val Arg Cys Glu His Ala Asp Leu
        35                  40                  45

Asp Ala
    50

<210> SEQ ID NO 3
<211> LENGTH: 57
<212> TYPE: PRT
<213> ORGANISM: Artificial Sequence
<220> FEATURE:
<223> OTHER INFORMATION: A modified human TGF-alpha sequence

<400> SEQUENCE: 3

Ser Leu Ser Leu Pro Ala Met Val Val Ser His Phe Asn Asp Cys Pro
1               5                   10                  15

Asp Ser His Thr Gln Phe Cys Phe His Gly Thr Cys Arg Phe Leu Val
            20                  25                  30

Gln Glu Asp Lys Pro Ala Cys Val Cys His Ser Gly Tyr Val Gly Ala
        35                  40                  45

Arg Cys Glu His Ala Asp Leu Leu Ala
    50                  55

<210> SEQ ID NO 4
<211> LENGTH: 11
<212> TYPE: PRT
<213> ORGANISM: Artificial Sequence
<220> FEATURE:
<223> OTHER INFORMATION: Modified human TGF alpha sequence fragment
<220> FEATURE:
<221> NAME/KEY: MISC_FEATURE
<222> LOCATION: (1)..(10)
<223> OTHER INFORMATION: Xaa at residue 1, 5, 7 to 9 is independently
      V, G or A;
<220> FEATURE:
<223> OTHER INFORMATION: Xaa at residue 6 is Y or F; and Xaa at residue
      10 is R or K

<400> SEQUENCE: 4

Xaa Cys His Ser Xaa Xaa Xaa Xaa Xaa Xaa Cys
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Modified human TGF alpha sequence fragment
<220> FEATURE:
<221> NAME/KEY: MISC_FEATURE
<222> LOCATION: (1)..(7)
<223> OTHER INFORMATION: Xaa at residue 1 and 4 is E or D; Xaa at
      residue 3 and 7 is V, G, or A; Xaa at residue 5 is L or I;
      and Xaa at residue 6 is D or E

<400> SEQUENCE: 5

Xaa His Xaa Xaa Xaa Xaa Xaa
1               5

<210> SEQ ID NO 6
<211> LENGTH: 18
<212> TYPE: PRT
<213> ORGANISM: Artificial Sequence
<220> FEATURE:
<223> OTHER INFORMATION: Modified human TGF alpha sequence fragment
```

```
-continued

<220> FEATURE:
<221> NAME/KEY: MISC_FEATURE
<222> LOCATION: (1)..(18)
<223> OTHER INFORMATION: Xaa at residue 1, 5, 7-9, 14, 18 is indep. V,
      G, or A; Xaa at
      residue 6 is Y or F; Xaa at residue 10 is R or K; Xaa at residue
      12, 15 is indep. E or D; Xaa at residue 16 is L or I; Xaa at
      residue 17 is D or E

<400> SEQUENCE: 6

Xaa Cys His Ser Xaa Xaa Xaa Xaa Xaa Cys Xaa His Xaa Xaa Xaa
1               5                   10                  15

Xaa Xaa

<210> SEQ ID NO 7
<211> LENGTH: 7
<212> TYPE: PRT
<213> ORGANISM: Artificial Sequence
<220> FEATURE:
<223> OTHER INFORMATION: Modified human TGF alpha sequence fragment
<220> FEATURE:
<221> NAME/KEY: MISC_FEATURE
<222> LOCATION: (1)..(7)
<223> OTHER INFORMATION: Xaa at residue 1 and 2 is indep. V, G, and
      A; Xaa at residue 7 is
      K or D

<400> SEQUENCE: 7

Xaa Xaa Ser His Phe Asn Xaa
1               5
```

TGF-α POLYPEPTIDES, FUNCTIONAL FRAGMENTS AND METHODS OF USE THEREFOR

CROSS REFERENCE TO RELATED APPLICATIONS

This application is a continuation of 09/641,587, filed Aug. 17, 2000 now abandoned, which is a continuation-in-part of U.S. Application 09/492,935, filed Jan. 27, 2000, which is a continuation-in-part of U.S. Application 09/378,567, filed Aug. 19, 1999 now abandoned, the disclosures of which are herein incorporated by reference in their entirety.

FIELD OF THE INVENTION

The present invention relates generally the field of tissue repair and more specifically to the use of transforming growth factor alpha (TGF-α) polypeptide, fragments and mimetics for stimulating stem cells proliferation, migration and differentiation.

BACKGROUND

Stem cells and tissue precursor cells play important roles in the development, regeneration and repair of organisms and particularly tissue and organs. Stimulation of tissue regeneration and repair can provide needed benefit to organisms suffering from injury, disorders or diseases which impair physiological functions increasing mortality and morbidity. For example, there are several disease treatments that could significantly benefit by having cells regenerate after injury or lesion formation. For example, in some instances, a particular treatment for a disease often detrimentally affects the subject being treated. One such example, is the administration of chemotherapeutic agents to subjects, which results in destruction of healthy cells, for example, cells of the gastrointestinal tract. Such chemotherapeutic agents include carmustine (BCNU), chlorambucil (Leukeran), cisplatin (Platinol), Cytarabine, doxorubicin (Adriaamycin), fluorouracil (5-FU), methoxetrate (Mexate), taxol, CPTI11, etoposide, and plicamycin (Mithracin) which are known for their direct stomatotoxic potential (Sonis, 1993, "Oral Complications in Cancer Therapy," In: Principles and Practice of Oncology, pp. 2385–2394, DeVitta et al., Eds., J. B. Lippincott, Philadelphia) and hence incidence of mucositis.

Oral mucositis is an example of a disorder resulting from the cytotoxic effects of chemotherapy and/or radiotherapy on the rapidly dividing epithelial cells of the oropharyngeal mucosa, and is exacerbated by infection with both endogenous oral flora and opportunistic bacterial and fungal pathogens. Complications related to oral mucositis vary in the different patient populations affected, but typically include pain, poor oral intake with consequent dehydration and weight loss, and systemic infection with organisms originating in the oral cavity. The pain associated with oral mucositis may be severe requiring narcotic analgesics, and the difficulty in eating can result in patients receiving total parenteral nutrition.

Accordingly, adult cell renewal via the differentiation of immature cells can help to alleviate the problems associated with tissue and cellular damage. For example, stimulating renewal of blood and lymphoid cell types by stimulating developmentally immature precursors (hematopoietic stem and progenitor cells) can assist in treating disorders associated with blood or lymphatic cell depletion.

While the hematopoietic system is the best understood self-renewing adult cellular system, it is believed that most, perhaps all, adult organs harbor precursor cells that under the right circumstances, can be triggered to replenish the adult tissue. For example, the pluripotentiality of neural crest cells and tissues of the adult gut contain immature precursors which replenish the differentiated tissue. The liver has the capacity to regenerate because it contains hepatic immature precursors. In addition, various epithelial cells, including cells of the skin renew due to proliferation and differentiation of stem cells. Through the mesengenic process, most mesodermal derivatives are continuously replenished by the differentiation of precursors. Such repair recapitulates the embryonic lineages and entails differentiation paths which involve pluripotent progenitor cells.

Mesenchymal progenitor cells are pluripotent cells that respond to specific signals and adopt specific lineages. For example, in response to bone morphogenic factors, mesenchymal progenitor cells adopt a bone forming lineage. For example, in response to injury, mesodermal progenitor cells can migrate to the appropriate site, multiply and react to local differentiation factors, consequently being induced down a distinct differentiation path. It has been suggested that the reason that limited tissue repair is observed in adults is because there are too few progenitor cells which can adopt specific differentiation lineages. It is clear that if such progenitor cells could be expanded tissue repair could be occur much more efficiently. In addition, an expanded pool of stem and progenitor cells, as well as non-terminally differentiated cells supplying a desired differentiation phenotype, would be of great value in transplantation and gene therapy as well as a myriad of therapeutic regimens.

SUMMARY OF THE INVENTION

The invention provides methods and compositions useful for expanding precursor cell and stem cells, including adult stem cell populations in vitro, in vivo, or ex vivo or a combination thereof. The methods and compositions are useful in treating a number of diseases, disorders or injuries by inducing the expansion, migration and differentiation of precursor cells, stem cells or adult stem cells.

In one embodiment, the invention provides a method for protection of a tissue or an organ from damage by a cytotoxic agent or other injury causing agent or activity. The method includes administering an effective amount of a TGF-α polypeptide (SEQ ID NO:1), a TGF-α related polypeptide, a TGF-α57 polypeptide (SEQ ID NO:3), a functional fragment thereof or a mimetic thereof to the tissue or organ prior to, simultaneously with or subsequent to contacting the tissue or organ with the cytotoxic agent or the injury causing agent or activity. Tissues include gastrointestinal tissue, urogenital tissue, musculoskeletal tissue, nerve tissue, or cardiovascular tissue, for example.

In another embodiment, the invention provides a method for treating, regenerating or repairing a tissue of a subject in vivo. The method includes contacting a tissue with a TGF-α polypeptide, a TGF-α related polypeptide, a fragment or a mimetic thereof prior to, contemporaneously with, or subsequent to a tissue injury in an amount effective to induce stem cell or precursor cell proliferation, migration, or differentiation at the site of injury thereby treating, regenerating or repairing the tissue. Contacting may be as a continuous infusion or by a bolus or single administration, for example.

In yet another embodiment, the invention provides a method for treating or preventing mucositis of the gastrointestinal tract in a subject The method includes administering a TGF-α polypeptide, a TGF-α related polypeptide, a TGF-α57 polypeptide, a fragment thereof, or a mimetic thereof in an amount effective to treat, inhibit or prevent gastrointestinal mucositis in the subject.

In another embodiment, the invention provides a method for expansion of a precursor cell, stem cell, or adult stem cell by recombinantly expressing within the cell an amount of a TGF-α polypeptide, a TGF-α related polypeptide, a functional fragment thereof, or a mimetic thereof effective to induce proliferation of the cell; and culturing the cells under conditions such that the cell proliferates.

In another embodiment, the invention provides a method for expansion of a hematopoietic precursor cell, an epithelial precursor cell, or a liver precursor cell, for example. The method includes recombinantly expressing within the cell an amount of a TGF-α polypeptide, a TGF-α related polypeptide, a functional fragment thereof, or a mimetic thereof effective to induce proliferation of the cells; and culturing the cell under conditions such that the cell proliferates. Preferably, the precursor cell is a human cell.

In another embodiment, the invention provides a method for promoting mammalian neuronal cell growth by contacting a mammalian neuron in vitro with a TGF-α polypeptide, a TGF-α related polypeptide, a functional fragment thereof, or a mimetic thereof effective to induce proliferation of the cells; and culturing the cells under conditions such that the cell proliferates.

In yet another embodiment, the invention provides a method for expanding stem cells ex vivo. The method includes culturing stem cells from a subject and contacting the stem cell culture with a TGF-α polypeptide, a TGF-α related polypeptide, a functional fragment thereof, or a mimetic thereof in an amount necessary to augment stem cell growth.

In another embodiment, the present invention provides a method for treating Type I or Type II diabetes by expanding a subject's population of insulin-producing cells. The method includes administering an effective amount of a TGF-α polypeptide (SEQ ID NO:1), a TGF-α related polypeptide, a TGF-α57 polypeptide (SEQ ID NO:3), a fragment thereof, or a mimetic thereof in an amount effective to expand the population of insulin-producing cells.

Also provided is a method for treating AIDS and HIV infection by increasing a subject's population of CD4+ T cells. The method includes administering an effective amount of a TGF-α polypeptide (SEQ ID NO:1), a TGF-α related polypeptide, a TGF-α57 polypeptide (SEQ ID NO:3), a fragment thereof, or a mimetic thereof.

DETAILED DESCRIPTION OF THE INVENTION

The present invention also provides compositions containing TGF-α polypeptides, a TGF-α related polypeptide, mimetic, or a fragment having TGF-α activity as well as polynucleotides encoding the polypeptides and fragments thereof. In addition, the invention provides methods of using the polypeptides and polynucleotides of the invention for treating or preventing a number of diseases and disorders as well as stimulating stem cell proliferation.

TGF-α is a member of the epidermal growth factor (EGF) family and interacts with one or more receptors in the EGF-family of receptors. TGF-α stimulates the receptor's endogenous tyrosine kinase activity which results in activating various cellular functions, such as stimulating a mitogenic or migration response in a wide variety of cell types. TCF-α and EGF mRNAs reach their highest levels and relative abundance (compared to total RNA) in the early postnatal period and decrease thereafter, suggesting a role in embryonic development. From a histological perspective, TGF-α is found in numerous cell types and tissues throughout the body. The active form of TGF-α is derived from a larger 30–35 kD precursor and contains 50 amino acids. Human TGF-α shares only a 30% structural homology with the 53-amino acid form of EGF, but includes conservation and spacing of all six cysteine residues. TGF-α is highly conserved among species. For example, the rat and human polypeptides share about 90% homology compared to a 70% homology as between the rat and human EGF polypeptide. The amino acid sequence of human TGF-α is shown in SEQ ID NO:1. TGF-α shares cysteine disulfide bond structures with a family of TGF-α related proteins including vaccinia growth factor, amphiregulin precursor, betacellulin precursor, heparin binding EGF-like growth factor, epiregulin (rodents), HUS 19878, myxomavirus growth factor (MGF), Shope fibroma virus growth factor (SFGF), and schwannoma derived growth factor. Such TGF-α related polypeptides are also useful in the methods of the invention.

TGF-α is an acid and heat stable polypeptide of about 5.6 kDa molecular weight. It is synthesized as a larger 30–35 kDa molecular weight glycosylated and membrane-bound precursor protein wherein the soluble 5.6 kDa active form is released following specific cleavage by an elastase-like protease. TGF-α binds with high affinity in the nanomolar range and induces autophosphorylation of one or more members of EGF receptor family (e.g., ErbB1 through 4 or receptors that bind a neuregulin ligand) to transduce subsequent signal pathways with the EGF receptors. TGF-α is 50 amino acids in length and has three disulfide bonds to form its tertiary configuration. TGF-α is stored in precursor form in alpha granules of some secretory cells.

Figure 1:
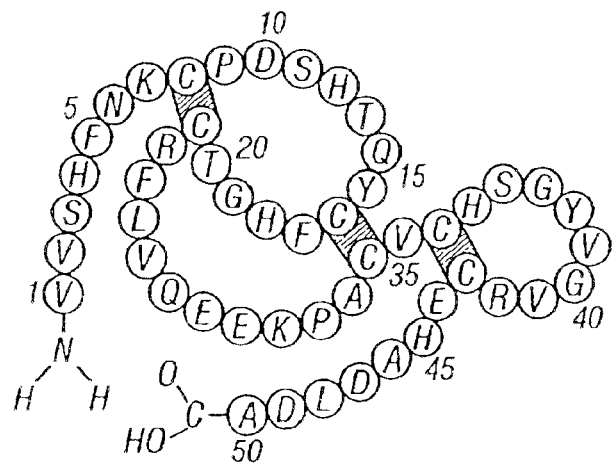
FIG. 1 shows the structure of rat TGF-α polypeptide and its 50 amino acids arranged into three loops (SEQ ID NO:2). The human TGF-α sequence is provided in SEQ ID NO:1 with a similar tertiary structure and a close sequence homology.

Human TGF-α is a polypeptide of 50 amino acids. The corresponding rat sequence is shown in FIG. 1. The human or rat TGF-α polypeptide can be divided roughly into three loop regions corresponding roughly (starting at the N terminus) to amino acids 1–21, to amino acids 16–32, and to amino acids 33–50. As discussed more fully below, the invention provides functional fragments of TGF-α that retain TGF-α biological activity. "Functional fragment" as used herein means a TGF-α peptide that is a fragment or a modified fragment of a full length TGF-α polypeptide or related polypeptide so long as the fragment retains some TGF-α related biological activity (e.g., interacts with an EGF family receptor, stimulates proliferation, migration, and/or differentiation of stem cells, or is useful for treating or preventing cachexia). Other biological activities associated with the polypeptides of the invention include, for example, mitogenic effects on stem cells and their more differentiated progeny of various tissues (e.g., epithelial stem cells, hematopoietic stem cells, neural stem cells, liver stem cells, keratinocyte stem cells, and pancreatic derived stem cells).

The invention provides methods of using TGF-α, related polypeptides and peptide fragments thereof as disclosed herein to stimulate stem cell proliferation, stimulate hematopoiesis in subjects undergoing cytotoxic cancer chemotherapy, to act as a cytoprotective agents and in treatments for subjects at risk of or having weight-loss disorders associated with cancer cytotoxic therapy. Such disorders include gastrointestinal (GI) mucositis, which can result from cytotoxic therapy. While not wanting to be bound to a particular theory, it is believed TGF-α may alleviate GI mucositis, in part, through its mitogenic effect on GI epithelial stem cells.

The present invention provides methods for the expansion of non-terminally differentiated cells ("precursor cells") by contacting a precursor cell or a population of precursor cells with a TGF-α polypeptide, a TGF-α related polypeptide, mimetic, or a fragment having TGF-α activity, and stimulating the precursor cells to proliferate, migrate and/or differentiate. In one embodiment, precursor cells are stimulated to proliferate while differentiation is inhibited. As used herein, a "precursor cell" includes any non-terminally differentiated cell. Precursor cells are typically stem cells or progenitor cells, including adult stem cells or adult progenitor cells. The invention is also directed to methods for the expansion of precursor cells by contacting the cells with a TCF-α polypeptide, a TGF-α related polypeptide, mimetic, or a fragment having TGF-α activity, such that the precursor cells are stimulated to proliferate, migrate and/or differentiate or differentiation of the precursor cell is inhibited without affecting the mitotic activity of the cell. Further, the precursor cells can be isolated from a cell population, if desired, before or after contacting with a TGF-α polypeptide, a TGF-α related polypeptide, mimetic, or a fragment having TGF-α activity. Contacting the cells with a TGF-α polypeptide, a TGF-α related polypeptide, mimetic, or a fragment having TGF-α activity is typically achieved by contacting the cell directly, e.g., soluble form or recombinantly expressed by a cell or immobilized on a solid surface, or by introducing into the cell a recombinant nucleic acid expressing a TGF-α polypeptide, a TGF-α related polypeptide, mimetic, or a fragment having TGF-α activity.

The invention also provides a class of peptides, including TGF-α and those smaller than the 50 amino acid human TGF-α, yet retaining TGF-α biological activity, which are useful as pharmacologic and therapeutic agents. Other polypeptides or fragments thereof include TGF-related polypeptides that have the biological activity of TGF-α (e.g., amphiregulin, vaccinia growth factor, myxomavirus growth factor (MCF), Shope fibroma virus growth factor (SFGF), heparin-binding EGF-like growth factor (HB-EGF)).

The least differentiated cell in a cell lineage is termed a stem cell. However, "stem cell" is an operational term. The classic definition of the stem cell is a cell which can divide to produce another stem cell (self-renewal capacity), as well as a cell which can differentiate along multiple specific differentiation paths. A stem cell is not a lineage restricted cell but is a cell that can be induced to differentiate down a lineage restricted path. It is often the case that a particular cell within a differentiation lineage, has derived from a "less" differentiated parent and can still divide and give rise to a "more" differentiated cellular progeny.

A "precursor cell" or "progenitor cell" has specific biochemical properties, may or may not divide and can be triggered to adopt a different differentiation state but not necessarily a fully differentiated state, by responding to specific developmental signals. The terms "precursor cell" and "stem cell" are often used interchangeably herein. The stem cells can be any stem cells or tissue precursor cells as described below.

Stem cell or precursor cells that can be stimulated in vivo to proliferate, migrate and/or differentiate when contacted by a TGF-α polypeptide, a related polypeptide, mimetic, or functional fragment thereof having TGF-α activity, include adult stem cells and precursor cells. Such stem cells and precursor cells include, for example, cells of neuronal tissue, urogenital tissue (e.g., kidney tissue), gastrointestinal tissue, musculoskeletal tissue, cardiovascular tissue, epithelial (e.g., keratinocyte precursor cells, intestinal precursor cells), and endothelial cells. Stem and precursor cells are discussed more fully below with respect to their location, properties, as well as methods of isolation.

TGF-α has recently been identified as useful for treating subjects with neurological deficits. The mechanism of action is thought to include stimulation, proliferation and migration of stem cells of neural origin to sites or lesions in a deficit. For example, Parkinson's Disease is characterized by resting tremor, rigidity, inability to initiate movement (akinesia) and slowness of movement (bradykinesia). The motor deficits are associated with progressive degeneration of the dopaminergic innervation to the nucleus accumbens and degeneration of noradrenergic cells of the locus ceruleus and serotonergic neurons of the raphe. Up to 80% of nigral dopamine neurons can be lost before significant motor deficits are manifest TGF-α, when infused into rat brains over a period of time (e.g., days or weeks), is useful for the treatment of neurodegenerative disorders. Intracerebroventricular (ICV) or intrastriatal infusions of TGF-α over a period of 18 days induced neuronal stem cell proliferation, but degenerating, damaged or otherwise abnormal cells are present to facilitate migration of the neuronal stem cells to a site of injury on a scale sufficient to impact recovery from an associated neurological deficit (see PCT publication WO 99/06060, incorporated herein by reference in its entirety). Forebrain neural stem cells migrate and affect treatment and recovery from a neurological deficit disorder including, for example, Parkinson's Disease, Huntington's Disease, Alzheimer's Disease and the like.

As used herein, a polynucleotide or a nucleic acid sequence refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions.

In addition, the polynucleotides or nucleic acid sequences may contain one or more modified bases. Thus, DNAs or RNAs with backbones modified for stability or for other reasons are "polynucleotides" as that term is intended herein Moreover, DNAs or RNAs comprising unusual bases, such as inosine, or modified bases, such as tritylated bases, to name just two examples, are polynucleotides as the term is used herein.

Nucleic acid sequences can be created which encode a fusion protein (e.g., a TGF-α polypeptide and another polypeptide, such as a targeting sequence) and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of a polynucleotide sequence. Both constitutive and inducible promoters, are included in the invention (see e.g., Bitter et al., Methods in Enzymology 153:516–544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention. Tissue-specific regulatory elements may be used. Including, for example, regulatory elements from genes or viruses that are differentially expressed in different tissues. For example, a variety of promoters have been identified which are suitable for up regulating expression in cardiac tissue. Included, for example, are the cardiac I-myosin heavy chain (AMHC) promoter and the cardiac I-actin promoter. Other examples of tissue-specific regulatory elements include, tissue-specific promoters, such as milk-specific (whey), pancreatic (insulin or elastase), actin promoter in smooth muscle cells or neuronal (myelin basic protein) promoters such as GFAP (specific for glial cells; see also U.S. Pat. No. 6,066,7260). Tissue specific promoters include the 5' or 3' flanking sequences of the beta-globin, elastase, alpha-fetoprotein, alpha-α crystalline, an erythroid specific transcriptional element and insulin genes (Yee, et al., Proc. Natl. Acad. Sci., U.S.A. 86:5873–5877, 1989; Swift, et al., Cell 38:639, 1984; Storb et al., Nature (Lond.) 310:238; Grosscheldl et al., Cell 41:885, 1985; Shani, Nature (Lond) 314:238, 1985; and Chada et al., Nature (Lond), 1985). In a another embodiment suitable promoters and/or enhancers may be selected from mammary gland specific genes which are normally only expressed in milk, for example the genes encoding α-casein (Gene Pharming, Leiden, Netherlands), β-casein (Genzyme Transgenics Corp. Framingham, Mass.), γ-casein, κ-casein, α-lactalbumin, β-lactalbumin, β-lactogloblin (PPL Therapeutics Ltd, Edinburgh, Scotland) and whey acidic protein (Altra Bio Inc., Arden Hills Minn.). Methods for targeting recombinant gene expression to the mammary gland of a mammal are described, for example, in U.S. Pat. No. 5,304,489.

A nucleic acid sequence of the invention including, for example, a polynucleotide encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a polynucleotide sequence encoding a TGF-α polypeptide, related polypeptides, fragments or mimetics thereof having a sequence as set forth in SEQ ID NO:1, 2, 3, 4 or 6 or fragment thereof (as described more fully below). The expression vector typically contains an origin of replication, a promoter, as well as specific genes which allow phenotypic selection of the transformed cells. Vectors suitable for use in the invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a polynucleotide encoding a polypeptide or a polypeptide fragment of the invention such that the localization or signal peptide is located at the amino terminal end of a resulting polypeptide. The construction of expression vectors and the expression of genes in transfected cells involves the use of molecular cloning techniques also well known in the art. (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., Molecular Cloning A Laboratory Manual, Cold Spring Harbor Laboratory, N.Y., 1989).

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a polynucleotide molecule encoding a TGF-α polypeptide, a TGF-α related polypeptide, mimetic, or a fragment having TGF-α activity (e.g., a functional fragment as set forth in SEQ ID NO:4, as described below).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be co-transfected with DNA sequences encoding a TGF-α polypeptide, mimetic or fragment and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, a polynucleotide encoding a TGF-α polypeptide, a TGF-α related polypeptide, mimetic, or a fragment having TGF-α activity may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a TGF-α polypeptide or fragment thereof in infected hosts (e.g., see Logan & Shenk, Proc. Natl. Acad. Sci. USA, 81:3655–3659, 1984). Alternatively, the vaccinia virus 7.5K promoter may be used. (e.g., see, Mackett, et al., Proc. Natl. Acad. Sci. USA, 79:7415–7419, 1982; Mackett, et al., J. Virol. 49:857–864,1984; Panicali, et at., Proc. Natl. Acad. Sci. USA 79:4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. High level expression may also be achieved using inducible promoters, including, but not limited to, the metallothionine IIA promoter and heat shock promoters.

For long-term, high-yield production of recombinant TGF polypeptides, mimetics and functional fragments, stable expression is preferred. Rather than using expression vectors which contain viral origins of replication, host cells can be transformed with the cDNA encoding a TGF-α polypeptide, mimetic or functional fragment controlled by appropriate expression control elements (e.g., promoter, enhancer, sequences, transcription terminators, polyadenylation sites, etc.), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including, but not limited to, the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817 1980) genes can be employed in tk-, hgprt- or aprt-cells respectively. Also, anti-metabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981); neo, which confers resistance to the aminoglycoside G-418 (Colberre-Garapin, et al., J. Mol. Biol. 150: 1, 1981); and hygro, which confers resistance to hygromycin (Santerre, et al., Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (omithine decarboxylase) which confers resistance to the omithine decarboxylase inhibitor, 2-(difluoromethyl)-DL-omithine, DFMO (McConlogue L., In: Current Communications in Molecular Biology, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature.

A polypeptide or protein refers to a polymer in which the monomers are amino acid residues which are joined together through amide bonds. When the amino acids are alpha-amino acids, either the L-optical isomer or the D-optical isomer can be used, the L-isomers being typical. A TGF-α polypeptide, a related polypeptide, mimetic, or functional fragment thereof is intended to encompass an amino acid sequence, including modified sequences such as glycoproteins, which exhibit TGF-α activity. The molecules (e.g., polypeptides) of the invention encompass amino acid sequences of human TGF-α as shown in SEQ ID NO:1 as well as polypeptides that have structural and/or functional characteristics of TGF-α. For example, a polypeptide or a TGF-α related polypeptide of the invention may include a polypeptide that shares a cysteine disulfide bond structure similar to TGF-α, such as a related family of proteins including vaccinia growth factor, amphiregulin precursor, betacellulin precursor, heparin binding EGF-like growth factor, epiregulin (rodent only), HUS 19878, myxomavirus growth factor (MGF), Shope fibroma virus growth factor (SFGF), and schwannoma derived growth factor. In addition, a molecules (e.g., a polypeptide) of the invention will have one or more functional characteristics related to TGF-α including, for example, the ability to interact with an EGF family receptor member, stimulate proliferation or migration of stem cells, or to treat or prevent cachexia.

The polypeptides of the invention are intended to cover substantially purified naturally occurring proteins, as well as those which are recombinantly or synthetically synthesized. In addition, a TGF-α or related polypeptide can occur in at least two different conformations wherein both conformations have the same or substantially the same amino acid sequence but have different three dimensional structures so long as the have a biological activity related to TGF-α. Polypeptide or protein fragments of TGF-α are also encompassed by the invention such as those described below (e.g., by formulas I, II, and III). Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general polypeptides of the present invention include peptides, or full length protein, that contain substitutions, deletions, or insertions into the protein backbone, that would still have an approximately 50%–70% homology to the original protein over the corresponding portion. A yet greater degree of departure from homology is allowed if like-amino acids, i.e. conservative amino acid substitutions, do not count as a change in the sequence. A TGF-α polypeptide fragments of the invention retains a biological activity associated with TGF-α as described above.

Homology to TGF-α polypeptide can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra). Such procedures and algorithms include, for example, a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra (D)-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on.

Solid-phase chemical peptide synthesis methods can also be used to synthesize the polypeptide or fragments of the invention. Such method have been known in the art since the early 1960's (Merrifield, R. B., J. Am. Chem. Soc., 85, 2149–2154 (1963) (See also Stewart, J. M. and Young, J. D., Solid Phase Peptide Synthesis, 2 ed., Pierce Chemical Co, Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al., Proc. Natl. Acad. Sci., USA, 81, 3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i. e, inverting and inserting the rod and pin tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. For example, if the peptide is from formula I or formula II (see below), a preferred means for synthesizing peptides of 10–18 amino acids in length is by direct peptide synthesis generally starting with the N-terminal amino acid and adding amino acids in the C terminal direction. TGFα has been made using recombinant techniques and is available as a laboratory reagent commercially. The bifunctional compounds of formula III are best synthesized with each loop peptide moiety synthesized and then added to the heterocyclic nitrogen atom using standard heterocyclic addition synthesis.

The invention provides a TGF-α polypeptide, a related polypeptide, mimetic, or functional fragment thereof having TGF-α. activity. The functional fragments and mimetics have an altered (compared to the naturally occurring molecule) sequence, for example, the N-terminal region of TGF-α (defined as the first seven N-terminal amino acids before the first loop region) and an altered "tail" region (defined as the last seven amino acids at the C-terminus after the third loop region) can be modified, truncated or deleted as described more fully herein. The alterations to the fifty amino acid sequence of human TGF-α (SEQ ID NO:1) caused by deletion of some or all of the seven amino acids at the N-terminal region resulted in a polypeptides having about 90% of the biological activity of the TGF-α. having a sequence as set forth in SEQ ID NO:1. In addition, substitution of D amino acids for natural L amino acids in the N-terminal region results in retention of TGF-α biological activity and an increase in plasma half life of the polypeptide after intravenous administration. Truncation of the N-terminus by 6 residues leaves a Lys residue at amino acid position 7 which provides for two free amino groups. This provides a site for forming a PEG (polyethylene glycol) "PEGalated TGFα mimetic" to be synthesized and further provides for improved pharmacokinetic benefits, including resistance to proteolytic enzyme breakdown.

In one embodiment, the TGF-α polypeptide, related polypeptide, mimetic or functional fragment is a TGF-α polypeptide as set forth in SEQ ID NO:1, SEQ ID NO:3, or a TGFα mimetic selected from the group consisting of formula I, formula II, formula III, formula IV, or formula V, wherein formula I is:

$$R_1\text{-}T\text{-}R_2 \qquad (I)$$

wherein $R_1$ is —$NH_2$, $R_1$ is $R_3$-$X_3$ wherein $R_3$ is a polyethylene glycol (PEG) attached to the free $NH_2$ moiety of $X_3$ (wherein $X_3$ is Lys or Arg) and having a molecular weight of PEG of from about 2000 daltons to about 10,000 daltons, or one or more of the following seven amino acids from formula VI, including either L (natural) or D chiral amino acids:

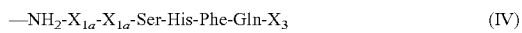
$$\text{—}NH_2\text{-}X_{1a}\text{-}X_{1a}\text{-Ser-His-Phe-Gln-}X_3 \qquad (IV)$$

wherein $X_1$ is independently Val, Gly or Ala and $X_3$ is Lys or Arg; wherein T is the native sequence of human TGFα (SEQ ID NO:1) from amino acid residue no. 8 (Cys) to amino acid residue no. 44 (Cys) consisting of native L amino acids; and wherein $R_2$ is —COOH or one or more of the following seven amino acids, including either L (natural) or D chiral orientations, from formula V:

$$\text{-}X_4\text{-His-}X_{1c}\text{-}X_4\text{-}X_5\text{-}X_6\text{-}X_{1c} \qquad (V)$$

wherein $X_4$ is Glu or Asp, wherein $X_5$ is Leu or Ile, wherein $X_6$ is Asp or Glu, and wherein $X_1$ is independently Val, Gly or Ala.

The invention provides a peptide having TGFα biological activity, comprising at least an 11-membered peptide compound of formula II (SEQ ID NO:4):

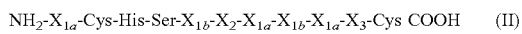
$$NH_2\text{-}X_{1a}\text{-Cys-His-Ser-}X_{1b}\text{-}X_2\text{-}X_{1a}\text{-}X_{1b}\text{-}X_{1a}\text{-}X_3\text{-Cys COOH} \qquad (II)$$

wherein $X_1$ is independently Val, Gly or Ala, wherein $X_2$ is Tyr or Phe, wherein $X_3$ is Arg or Lys, and wherein the two Cys moieties form a disulfide bond to create an 11-amino acid functional peptide having a 10 member loop structure. In addition, at least one or more of the following amino acids of formula III (SEQ ID NO:5) may be added to the C terminus Cys moiety of formula I (SEQ ID NO:4):

$$\text{-}X_4\text{-His-}X_{1c}\text{-}X_4\text{-}X_5\text{-}X_6\text{-}X_{1c} \qquad (III)$$

wherein $X_4$ is Glu or Asp, wherein $X_5$ is Leu or Ile, and wherein $X_6$ is Asp or Glu. Preferably, $X_{1a}$, is Val, $X_{1b}$ is Gly and $X_{1c}$ is Ala thereby producing an 11, 12, 13, 14,15, 16, 17 or 18 amino acid peptide. Preferably, $X_2$ is Tyr, and $X_3$ is Arg. Accordingly, in one embodiment the functional peptide of the invention has a sequence:

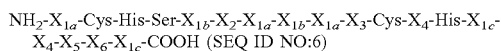
$$NH_2\text{-}X_{1a}\text{-Cys-His-Ser-}X_{1b}\text{-}X_2\text{-}X_{1a}\text{-}X_{1b}\text{-}X_{1a}\text{-}X_3\text{-Cys-}X_4\text{-His-}X_{1c}\text{-}$$
$$X_4\text{-}X_5\text{-}X_6\text{-}X_{1c}\text{-COOH (SEQ ID NO:6)}$$

SEQ ID NO:6 forms a 10 member loop structure with a 7 member tail that can be varied in length. In addition, SEQ ID NO:6 can form dimers comprising, for example, a 34-mer peptide. Accordingly, the functional peptide can be from about 10 to 18 amino acids in length (e.g., 10, 11, 12, 13, 14, 15, 16, 17, or 18 amino acids) wherein $X_{1a}$ is Val, $X_{1b}$ is Gly, $X_{1c}$ is Ala and $X_4$ is Gly and may also comprise hetero- or homo-dimers of various TGF-α peptides described herein. Such dimers may have greater or reduced activities as compared to monomers.

The invention further provides an active TGF-α57 polypeptide (SEQ ID NO:3), wherein TGF-α57 is a 57 amino acid polypeptide having the formula VI:

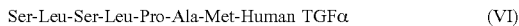

Ser-Leu-Ser-Leu-Pro-Ala-Met-Human TGFα    (VI)

wherein human TGFα is a 50 amino acid polypeptide having a sequence as set forth in SEQ ID NO:1.

By "functional" as used in connection with the peptides or peptide fragments of the invention is meant that the peptides or fragments have TGF-α activity. This biological activity is associated with the peptides of formula I, formula II and formula III and the data available for TGFα.

The functional peptides of the invention are based, in part, upon the discovery that a loop peptide of TGF-α exhibits TGF-α biological activity and can therefore stimulate multipotent precursor cells to divide and migrate. This activity indicates that the loop peptide is effective to treat a number of diseases and disorder associated with tissue damage or injury including, for example, neurological deficits caused by a wide variety of diseases and injuries that each result in a neurological deficit in some specific area of the brain or specific kind of neuron. These include degenerative diseases, such as Alzheimer's Disease (AD), Parkinson's Disease (PD), and Huntington's Disease (HD), Pick's disease, progressive supranuclear palsy, striatonigral degeneration, cortico-basal degeneration, olivopontocerebellar atrophy, Leigh's disease, infantile necrotizing encephalomyelopathy, Hunter's disease, mucopolysaccharidosis, various leukodystrophies (such as Krabbe's disease, Pelizaeus-Merzbacher disease and the like), amaurotic (familial) idiocy, Kuf's disease, Spielmayer-Vogt disease, Tay Sachs disease, Batten disease, Jansky-Bielschowsky disease, Reye's disease, cerebral ataxia, chronic alcoholism, beriberi, Hallervorden-Spatz syndrome, cerebellar degeneration, and the like.

Accordingly, in one embodiment, a TGF-α polypeptide, fragment or mimetic can be used to treat, repair or regenerate a tissue or a subject having an injury. In one embodiment, the invention provides a continuous infusion of a TGF-α polypeptide, a related polypeptide, mimetic, or functional fragment thereof having TGF-α activity at the site of injury or at a site that allows for delivery of the TGF-α polypeptide, fragment or mimetic to the site of injury (e.g., a vein or portal upstream of the injured site). The TGF-α polypeptide, a related polypeptide, mimetic, or functional fragment thereof having TGF-α activity of the invention delivered to the site of injury promotes stem cell proliferation, migration, and/or differentiation of stem cells or precursor cells at the site of injury and thus promotes tissue repair and regeneration. Any number of tissues can be treated, repaired or regenerated, including kidney tissue, liver tissue, spleen tissue, bone tissue, neural tissue, skin tissue, gastrointestinal tissue, urogenital tissue, and musculoskeletal tissue. It is contemplated that certain tissues may be excluded from the invention (e.g., brain tissue). For example, administration or delivery of a TGF-α polypeptide, a TGF-α related polypeptide, mimetic, or a fragment having TGF-α activity at the site of injury within the gastrointestinal tract results in a renewal and regeneration of the villi and epithelial cells lining the gastrointestinal tract. In addition, similar results were seen in kidney and spleen tissues.

Further, injuries (traumatic or neurotoxic) that cause a loss of neuronal function can be treated by the functional polypeptides and mimetics of the invention. Reid et al. describes the continuous infusion of TCF-α into brain tissue following injury (see, WO 99/06060, and U.S. patent application Ser. No. 09/129,028 which are incorporated herein by reference in their entirety). The present invention describes methods whereby continuous infusion into various injured tissues or bolus delivery of a TGF-α polypeptide, a TGF-α related polypeptide, mimetic, or a fragment having TGF-α activity either before, prior to, simultaneous with or following tissue injury can stimulate stem cells in the damaged or injured tissue to proliferate, migrate from tissue adjacent to the damaged tissue, and differentiate to replace or repair cells at the site of injury.

Injuries treatable by the methods of the invention include, for example, gunshot wounds, injuries caused by blunt force, penetration injuries, injuries caused by surgical procedure (e.g., tumor removal, abscess removal, epilepsy lesion removal) poisoning (e.g., carbon monoxide), shaken baby syndrome, adverse reactions to medications, drug overdoses, and post-traumatic encephalopathy. Ischemia can further cause CNS injury due to disruption of blood flow or oxygen delivery that can kill or injure neurons and glial cells (e.g., TGF-α confers protection from ischemia in a porcine gastrointestinal model and a family member, Heparin-binding EGF, confers protection from ischemia in a rat stroke model). Such injuries can be treated by administration of the functional peptides and include, for example, injuries caused by stroke, anoxia, hypoxia, partial drowning, myoclonus, severe smoke inhalation, dystonias, and acquired hydrocephalus Developmental disorders that can be treated by the functional peptides include, for example, schizophrenia, certain forms of severe mental retardation, cerebral palsey, congenital hydrocephalus, severe autism, Downs Syndrome, LHRH/hypothalamic disorder, and spina bifida. The functional peptides can be further used to treat disorders affecting vision caused by the loss or failure of retinal cells and include, for example, diabetic retinopathy, serious retinal detachment (associated with glaucoma), traumatic injury to the retina, retinal vascular occlusion, macular degeneration, optic nerve atrophy and other retinal degenerative diseases. Injuries to the spinal cord can be treated by the functional peptides. Examples of spinal cord injuries are post-polio syndrome, amyotrophic lateral sclerosis, traumatic injury, surgical injury, and paralytic diseases. Demylinating autoimmune disorders can be treated by administration of the functional peptides and include, for example, multiple sclerosis. The functional peptides can also be used to treat neurological deficits caused by infection of inflammatory diseases, including, for example, Creutzfeldt-Jacob disease and other slow virus infectious diseases of the CNS, AIDS encephalopathy, post-encephalitic Parkinsonism, viral encephalitis, bacterial meningitis and other CNS effects of infectious diseases.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or disorder or sign or symptom thereof, and/or may be therapeutic in terms of a partial or complete cure for a disorder or disease and/or adverse effect attributable to the disorder or disease. "Treating" as used herein covers any treatment of, or prevention of, or inhibition of a disorder or disease in a subject. The subject can be an invertebrate, a vertebrate, a mammal, and particularly a human, and includes by way of example: (a) preventing the disease or disorder from occurring in a subject that may be predisposed to the disease or disorder, but has not yet been diagnosed as having it; (b) inhibiting the disease or disorder, i.e., arresting its progression; or (c) relieving or ameliorating the disease or disorder, i.e., causing regression. Thus, treating as used herein includes, for example, repair and regeneration of damaged or injured tissue or cells at the site of injury or prophylactic treatments to prevent damage, e.g., before chemotherapy.

In another embodiment, a single bolus of a TGF-α polypeptide, a related polypeptide, mimetic, or functional fragment thereof, having TGF-α activity, is administered prior to, contemporaneously with, or subsequent to a tissue injury. Typically a single dose injection will be a few hours, a few days or a few weeks after tissue injury. The present invention is based in part upon the discovery that a TGF-α polypeptide, a related polypeptide, mimetic, or functional fragment thereof having TGF-α activity induces stem cell proliferation, migration, and/or differentiation at the site of tissue injury. A single unit dosage delivery can be immediately adjacent to the site of injury or can be, for example, to a vessel that drains or flows to the site of injury.

A TGF-α, TGFα57 polypeptide, related polypeptides, fragments thereof or a TGF-α mimetic is administered initially at a point in time prior to the time of damage of the target organ or tissue. In one embodiment, a TGF-α polypeptide, fragments, or mimetic is administered initially prior to administration of a cytotoxic agent.

In yet another embodiment, a single bolus of a TGF-α polypeptide, a related polypeptide, mimetic, or functional fragment thereof, having TGF-α activity, can be followed by subsequence administrations of a TGF-α polypeptide, a related polypeptide, mimetic, or functional fragment as continuous infusions or additional single bolus deliveries. In addition, it is contemplated that additional therapeutic agents can be combined with, administered prior to or subsequent to administration of a TGF-α polypeptide, a related polypeptide, mimetic, or functional fragment thereof.

In still another embodiment, a TGF-α polypeptide, a related polypeptide, mimetic, or functional fragment thereof having TGF-α activity are useful as vaccine adjuvants to increase mucosal humoral immunity. When a TGF-α57 polypeptide was administered to mice (10–50 μg/kg ip for 3 successive days or 10–50 μg/kg iv for 2 successive days or 10 μg/kg sc every day for 3–5 successive days) histological examination of lymphoid tissues such as spleen and the large intestine showed an increase in T cell progenitor cells. Histological staining showed increased T cell progenitors as compared with untreated mice and appeared as new germinal foci. Such T cell progenitors positioned in the gastrointestinal tract represent a reservoir for CD4 helper cells needed against mucosal directed vaccine production mediated by priming with exogenous antigen. The T cell progenitor cells appear to be double null and thus naive. Accordingly, the T cell progenitor cell response to TGF-α and TGF-α mimetics provides the utility for such compounds to provide a strong mucosal immunity response and usefulness as a mucosal vaccine and as a universal stem cell adjuvant.

During a course of therapy organs may be targeted by specific chemical agents, however, organ damage can be a side effect. In U.S. patent application Ser. No. 09/299,473 filed Apr. 26, 1999 now abandoned (the disclosure of which is incorporated by reference herein), the effects of increasing hematopoiesis based upon hematopoietic injury from cytotoxic cancer therapy is described. These data can be farther expanded to organ damage caused by chemicals known to cause specific organ damage. As shown below, gentamycin is an antibiotic known to cause kidney damage as a dose-limiting side effect. Histological data shows that the kidney damage seen in glomeruli of kidneys is alleviated by concurrent and subsequent administration of a TGF-α polypeptide (in this case a TGF-α57 polypeptide was used). Kidney damage can also occur following exposure to cancer chemotherapeutic agent, such as cis platinum, or gentamycin or the toxin from *E. coli* OH1:37 from undercooked contaminated meats. Intestinal damage can occur form many cancer chemotherapeutic agents, cholera toxin, and the like. Lungs can be damaged by the anti-cancer agent bleomycin. Accordingly, administration of a TGF-α polypeptide, fragments, or mimetic before, during and following exposure to an organ toxic agent can prevent organ damage.

In addition, administration of a TGF-α polypeptide, fragments, and mimetic to regenerate damaged tissue, for example, in kidney, an organ sensitive to such damage, is also disclosed herein. In an in vivo experiment, mice were administered 10 mg/kg of Cis-platinum as a single ip injection and treated mice administered 10 μg/kg a human TGF-α57 (R&D Systems, Minneapolis, Minn.). TGF-α57 was administered just before CP and in two additional doses after, by ip administration for a general systemic effect. Several organs or tissues were collected from the animals sacrificed 4 days after CP dose (or saline for no TGFα57) and tissues were examined histologically.

H&E stained kidney tissue (primarily glomeruli) that were exposed to the high kidney-damaging CP dose showed extensive damage to the glomerulus with a distortion in the architecture of Bowman's capsule. The cuboidal epithelium of the proximal convoluted tubule was also damaged. Kidneys from control animals exhibited normal morphology. Kidney from a mouse treated with CP and also with (10 μg/kg) TGF-α57 6 hours prior to CP and 24 and 48 hours after CP showed that TGF-α57 treatment essentially protected the glomeruli from damage.

In another set of in vivo experiments, gentamicin (antibiotic having dose-limiting kidney toxicity side effects) was used as the cytotoxic agent for a chronic cytotoxic agent. Eight CD-1 mice were weighed and injected subcutaneously with 80 mg/kg of gentamicin sulfate. Four of the mice were controls and injected with 0.1 ml of 0.9% saline and the other four injected ip with 0.1 ml of 10 μg/ml stock of TGF-α (57 aa polypeptide) as a 1 μg dose. The mice were reinjected with the same does of saline or TGF-α every 24 hours and every 24 hours subcutaneously with the same does of gentamicin. After two weeks of treatment, the mice were sacrificed and blood BUN and creatinine were measured and the kidneys examined. The average creatinine values were 0.49±0.096 for controls and 0.34±0.042 for treated mice. The average BUN values were 36.1±14.8 for controls and 35.5±4.9 for treated mice.

In another set of in vivo experiments, glycerol (50% (v/v) aqueous solution, Sigma) was used as the cytotoxic agent for an acute cytotoxic agent. Six CD-1 mice were weighed and injected into both hind limbs im with 10 ml/kg of 50% (v/v) glycerol, one half into each hind limb im. Three of the mice were controls and injected with 0.1 ml of 0.9% saline and the other three injected ip with 0.1 ml of 10 μg/ml stock of TGF-α (57 aa polypeptide) as a 1 μg dose. The nice were reinjected with the same does of saline or TGF-α the next day and another equal dose of 50% glycerol. After two treatments, the mice were sacrificed and blood BUN and creatinine was measured and the kidneys examined. The average creatinine values were 1.75±0.613 for controls and 1.51±0.940 for treated mice. The average BUN values were 1172.8±38.0 for controls and 165.3±75.6 for treated mice.

The invention includes various pharmaceutical compositions useful for delivery or administration of the polypeptides, peptides and mimetics of the invention. In one embodiment, the pharmaceutical composition are useful in managing or treating tissue damage and cell renewal in a subject. In another embodiment, the invention provides a method of treating or preventing weight-loss associated with a disorder or disease. Such disorders or diseases include weight-loss attributable to, for example, chemotherapy or a viral infection (e.g., HIV). The pharmaceutical compositions according to the invention are prepared by bringing a polypeptide or peptide derivative of TGF-α, a TGF-α mimetic into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories and including, for example, alginate based pH dependent release gel caps. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or by several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

In one embodiment, the invention provides a pharmaceutical composition useful for administering a TGF-α polypeptide or functional fragment, or a nucleic acid encoding a TGF-α polypeptide or functional fragment, to a subject in need of such treatment. "Administering" the pharmaceutical composition of the invention may be accomplished by any means known to the skilled artisan. Preferably a "subject" refers to a mammal, most preferably a human.

The TGF-α polypeptide or functional fragment can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water. Where the disease or disorder is a gastrointestinal disorder oral formulations or suppository formulations are preferred.

Sterile injectable solutions can be prepared by incorporating the active agent (see formula I, formula II, or formula III and TGFα) in the required amount (e.g., about 10 μg to about 10 mg/kg) in an appropriate solvent and then sterilizing, such as by sterile filtration. Further, powders can be prepared by standard techniques such as freeze drying or vacuum drying.

In another embodiment, the active agent is prepared with a biodegradable carrier for sustained release characteristics for either sustained release in the GI tract or for target organ implantation with long term active agent release characteristics to the intended site of activity. Biodegradable polymers include, for example, ethylene vinyl acetate, polyanhydrides, polyglycolic acids, polylactic acids, collagen, polyorthoesters, and poly acetic acid Liposomal formulation can also be used.

In another embodiment, infant formula comprising standard formula ingredients but supplemented with TGF-α, fragments thereof or mimetics thereof at a concentration of from about 400 μg/kg to about 4 mg/kg in the final formula are provided. TGF-α is a natural occurring small hormone like polypeptide that is found in human mother's milk. It is used by the body to maintain a daily need to regenerate the epithelial cells in the intestinal mucosa during remodeling (which takes place every 3–5 days). In addition, following GI injury, TGF-α and its receptor (EGF) are upregulated at the site of injury. TGF-α administration can accelerate mucosal repair and to protect mucosal damage caused by acid or aspirin. Moreover, knock-out mice that lack the ability to produce TGFα have their mucosal injury exacerbated. However, higher doses and concentrations are needed for oral delivery as opposed to parenteral administration.

The present invention further provides a method for expanding stem cells or precursor cells. In one embodiment, the stem cells or precursor cells are expanded ex vivo. One method of the invention comprises: culturing stem cells from a subject; adding TGF-α, a TGF-α57 polypeptide, a TGF-α mimetic, or a TGF-α functional fragment to the culture medium in an amount effective to augment stem cell growth.

The stem cells can be any stem cells or tissue precursor cells as described below. The precursor cells to be expanded or stimulated in vitro or in vivo. In one embodiment of the present invention the cells can be isolated from a variety of sources using methods known to one skilled in the art. The precursor cells can be of ectodermal, mesodermal or endodermal origin. Any precursor cells which can be obtained and maintained in vitro can potentially be used in accordance with the invention. In one embodiment, the precursor cell is a stem cell. Such stem cells include but are not limited to hematopoietic stem cells (HSC), stem cells of epithelial tissues such as the skin and the lining of the gut, embryonic heart muscle cells, and neural stem cells. The stem cells can be expanded under cell growth conditions, i.e., conditions that promote proliferation ("mitotic activity") of the cells.

The present invention is also directed to methods for expanding precursor cells in vitro and using the expanded precursor cells for grafting, cell therapy or gene therapy as well as for use in providing desired cell populations and for use in regenerating injured and/or diseased tissues. The expanded precursor cell populations can be administered to a subject using methods commonly known to those skilled in the art.

In one embodiment, the precursor cells are expanded in vitro and then delivered to a site or tissue in need of repair. Alternatively, the cells may be delivered in conjunction with various delivery vehicles, including biocompatible biodegradable or non-biodegradable sponges (e.g., collagen, or other extracellular matrix materials), cotton, polyglycolic acid, cat gut sutures, cellulose, gelatin, dextran, polyamide, a polyester, a polystyrene, a polypropylene, a polyacrylate, a polyvinyl, a polycarbonate, a polytetrafluorethylene, or a nitrocellulose compound formed into a three-dimensional structure (see, for example, U.S. Pat. No. 5,858,721 to Naughton et al., the disclosure of which is incorporated herein by reference).

In another embodiment, the precursor cells can be expanded in vitro and used in tissue engineering processes. For example, precursor cells can be expanded in vitro, applied to a three dimensional scaffold and the precursor cells contacted with various agents or parenchymal cells to induce differentiation down a particular cell type or tissue type. Alternatively, the cells can be expanded and cultured under physiological conditions that mimic the conditions of the tissue to be derived. Such methods include the culturing of precursor cells expanded with a transforming growth factor alpha or related protein within a bioreactor. Various bioreactor are known in the art and include bioreactors which mimic the environment of cardiovascular tissue to form tubes or tendons (U.S. Pat. No. 5,863,531), cartilage bioreactors (U.S. Pat. No. 5,928,945), liver bioreactor (U.S. Pat. No. 6,008,049).

In another embodiment, after expansion of the precursor population using a TGF-α polypeptide, fragment or mimetic, the precursor cell can be induced to differentiate in vivo, or alternatively in vitro, followed by administration to an individual, to provide a differentiated phenotype to a subject.

The invention is also directed to precursor cells expressing recombinant genes, such that the precursor cells express a desired gene. These recombinant precursor cells can be transplanted into a patient such that the desired gene is expressed in a subject to alleviate a disease state caused by the lack of expression of the recombinant gene. The precursor cells can be made recombinant either before or after precursor cell expansion using the TGF-α polypeptides, fragments and mimetics of the invention. Methods of transfecting the nucleic acid encoding the desired gene product such that the precursor cell or its progeny stably expresses the gene product are known to those of skill in the art and are described herein.

The subject into which the expanded cells or their progeny are introduced, or from which precursor cells can be derived, is preferably an animal, including but not limited to animals such as cows, pigs, horses, chickens, cats, dogs, etc., and is preferably a mammal, and most preferably a human.

In one embodiment of the invention, the subjects to which the expanded precursor cells are administered are immunocompromised or immunosuppressed or have an immune deficiency. For example, the subject has Acquired Immune Deficiency Syndrome (AIDS) or has been exposed to radiation or chemotherapy regimens for the treatment of cancer, and the subjects are administered hematopoietic or immune precursor cells such that the administered cells perform a needed immune or hematopoietic function. The expanded precursor cell is may be originally derived from the subject (i.e., autologous) or may be derived from a related subject (i.e., allogeneic) or may be from a different species (i.e., xenogeneic).

Precursor cells can be obtained by any method known in the art. The cells can be obtained directly from tissues of a subject or from cell lines or by production in vitro from less differentiated precursor cells, e.g., stem or progenitor cells. An example of obtaining precursor cells from less differentiated cells is described in Gilbert, 1991, Developmental Biology, 3rd Edition, Sinauer Associates, Inc., Sunderland Mass. Briefly, progenitor cells can be incubated in the presence of other tissues or growth and differentiation factors which cause the cell to differentiate. For example, when lung bud epithelium is cultured alone, no differentiation occurs. However, when lung bud epithelium is cultured with stomach mesenchyme or intestinal mesenchyme, the lung bud epithelium differentiates into gastric glands or villi, respectively. Further, if lung bud epithelium is cultured with liver mesenchyme or bronchial mesenchyme, the epithelium differentiates into hepatic cords or branching bronchial buds, respectively.

The following describes approaches for the isolation of precursor cells and precursor cell-containing tissues, which are to be contacted with a TGF-α polypeptide, fragment, or mimetic according to the present invention. As already mentioned, isolated cell types or mixed cell populations can be treated with a TGF-α polypeptide, fragment, or mimetic to expand the precursor population. The isolated precursor cell or precursor cell population can be cultured ex vivo for proliferation which under the influence of the polypeptides, fragments and mimetics allow for continued growth, i.e., expand, in order to reach the desired numbers. Once expanded the cells can be transplanted or used for production of autologous biological agents. Optionally, a recombinant gene can be introduced into the cell so that it or its progeny expresses a desired gene product before transplantation. Introduction of a recombinant gene can be accomplished either before or after precursor cell expansion.

In a one embodiment, the precursor cell populations are purified or at least highly enriched prior to contacting with a TGF-α polypeptide, fragment, or mimetic. However, in order to treat precursor cells it is not necessary that the precursor cells are a pure population. Consequently, the precursor population can still be expanded selectively. Furthermore, purification may not be necessary or desirable prior to therapeutic administration in vivo.

The isolation of precursor cells for use in the invention can be carried out by any of numerous methods commonly known to those skilled in the art. For example, one common method for isolating precursor cells is to collect a population of cells from a subject and using differential antibody binding, wherein cells of one or more certain differentiation stages are bound by antibodies to differentiation antigens, fluorescence activated cell sorting is used to separate the desired precursor cells expressing selected differentiation antigens from the population of isolated cells.

One type of progenitor cells used for therapeutic applications are those derived from the mesenchyme. Mesenchymal progenitors give rise to a very large number of distinct tissues (Caplan, J. Orth. Res 641–650, 1991). Most work to date involves the isolation and culture of cells which can differentiate into chondrocytes and osteoblasts. The systems developed to isolate the relevant progenitor cell populations were worked out first in chick embryos (Caplan, Exp. Cell. Res. 62:341–355, 1970; Caplan, 1981, 39th Annual Symposium of the Society for Developmental Biology, pp. 37–68; Caplan et al., 1980, Dilatation of the Uterine Cervix 79–98; DeLuca et al., J. Biol. Chem. 252:6600–6608, 1977; Osdoby et al., Dev. Biol. 73:84–102, 1979; Syftestad et al., Dev. Biol. 110:275–283, 1985). Conditions were defined under which chick mesenchymal cells differentiated into chondrocytes and bone. With regard to cartilage and bone, the properties of mouse or human mesenchymal limb appear to be quite similar if not identical (Caplan, J. Orth. Res. 641–650, 1991). Mesenchymal cells capable of differentiating into bone and cartilage have also been isolated from marrow (Caplan, J. Orth. Res. 641–650, 1991).

Caplan et al., U.S. Pat. No. 5,226,914 describes an exemplary method for isolating mesenchymal stem cells from bone marrow. These isolated marrow stem cells can be used in conjunction with a TGF-α polypeptide, fragment, or mimetic to expand the stem cell population. These expanded cells may then be transplanted into a subject where they can differentiate into osteocytes, cartilage, chondrocytes, adipocytes, etc., depending on the surrounding microenvironment of the transplant site. Alternatively, the expanded stem cells can be contacted in vitro prior to transplantation with agents which induce differentiation of the stems cells down a particular lineage.

It has been possible to purify marrow mesenchymal cells by their differential adhesion to culture dishes and demonstrate that they can differentiate, e.g., into osteoblasts. Expansion of such isolated stem cells using a TGF-α polypeptide, fragment, or mimetic can provide a source of cells which when transplanted to the appropriate sites will be induced by the microenvironment to differentiate into the appropriate lineage and help repair damaged and/or diseased tissue. It is expected that the animal models described to date will be applicable to humans. Indeed, as far as cartilage and bone are concerned, the properties of mouse and human limb mesenchymal cells in culture are quite similar, if not identical (Hauska, Dev. Biol. 37:345–368, 1974; Owens and Solursh, Dev. Biol. 88:297–311, 1981). The isolation of human marrow and the demonstration that cells deriving from it can sustain osteogenesis has been described, e.g., by Bab et al., Bone Mineral 4:373–386, 1988.

Several bone marrow isolation protocols have been reported and can be used to obtain progenitor or precursor cells. Single cell suspensions from rat bone marrow can be prepared according to Goshima et al., Clin. Orth. and Rel. Res. 262:298–311, 1991. Human stem cell cultures from marrow can be prepared as described by Bab et al., Bone Mineral 4:373–386, 1988, as follows: Whole marrow cells are obtained from a subject. The marrow samples are separated from either the iliac crest or femoral midshaft. Marrow samples, 3 ml in volume, are transferred to 6 ml of serum-free Minimal Essential Medium (MEM) containing 50 U/ml penicillin and 0.05 mg/ml streptomycin-sulfate. A suspension of predominantly single cells is prepared as described in Bab et al., Calcif. Tissue Int. 36:77–82, 1984; and Ashton et al., Calcif. Tissue Int. 36:83–86, 1984, by drawing the preparation into a syringe and expelling it several times sequentially through 19, 21, 23 and 25 gauge needles. The cells are counted using a fixed volume hemocytometer and the concentration adjusted to $1-5\times10^8$ total marrow cells per ml suspension. Positive and negative control cell suspensions can be set as described in Shteyer et al., Calcif. Tissue Int. 39:49–54, 1986, using rabbit whole marrow and spleen cells, respectively.

Adult neural precursors are generally located in the wall of the brain ventricles. It is thought that from these proliferative regions, neuronal precursors migrate towards target positions where the microenvironment induces them to differentiate. Studies have been reported where cells from the sub-ventricular zone can generate neurons both in vivo as well as in vitro, reviewed in Alvarez-Buylla and Lois, Stem Cells (Dayt) 13:263–272, 1995.

The neuronal precursors from the adult brain can be used as a source of cells for neuronal transplantation (Alvarez-Buylla, Proc. Natl. Acad. Sci. USA 90:2074–2077, 1993). Neural crest cells have also been long recognized to be pluripotent neuronal cells which can migrate and differentiate into different neuronal cell types according to the instructions they receive from the microenvironment they find themselves in (LeDouarin and Ziller, Curr. Opin. Cell Biol. 5:1036–1043, 1993). In addition, neurogenesis has been shown to occur in the hippocampus, olfactory bulb and epithelium and that endogenous neural precursors can be induced in situ to differentiate into mature neurons in response to signaling molecules, in regions of adult mammalian neocortex that do not normally undergo any neurogenesis (Magavi et al., Nature, 405:951–955 (2000)).

Neural stem cells have been found in subependyma throughout the adult rodent CNS (Ray et al. Soc. Neurosci, 22:394.5, 1996) and in the subependyma of adult human forebrain (Kirschenbaum et al., Cerebral Cortex 4:576–589, 1994). Thus, the discovery that TGF-α stimulates proliferation of neural stem cells and promotes migration to a site of injury or deficit has led to its investigation for the treatment of a neurodegenerative disorder (Alzheimer's Disease, Huntington's Disease and Parkinson's Disease) or CNS traumatic injury (e.g., spinal chord injury), demyelinating disease, CNS inflammatory disease, CNS autoimmune disease (e.g., multiple sclerosis) and CNS ischemic disease (e.g., stroke or brain attack).

A CNS stem cell has the potential to differentiate into neurons and astrocytes as well as self replication and thus self renewal. Both neuronal and glial cells are derived from a common precursor cell. In the vertebrate CNS, pluripotential cells have been identified in vitro and in vivo. Certain mitogens, such as TGF-α, can cause proliferation of CNS pluripotential cells in vitro. Thus, it is possible to harvest such cell from a subject, treat them ex vivo to stimulate proliferation in culture and then readminister the cells back to a subject. Immunohistochemical analysis in the human brain supports the notion that TGF-α and its 35 kD precursor are widely distributed in neurons and glial cells both during development and during adulthood. In TGF-α knockout mice genetically altered to lack expression of functioning TGF-α, there was a decrease in neural progenitor cell proliferation in forebrain subependyma, providing evidence for TGF-α as a proliferative factor for neural progenitor cells.

TGF-α is found mainly in various neurons of the CNS during development and in the adult brain in the cerebral neocortex, hippocampus and striatum. It is also found in glial cells, primarily in the cerebral and cerebellar cortex areas. Northern blot analyses showed that TGF-α but not EGF (epidermal growth factor) is the most abundant ligand that binds to one or more of the EGF receptor family in the brain. TGF-α mRNA levels were 15–170 times higher than EGF in cerebellum and cerebral cortex. TGF-α also appears in germinal centers of the brain during neurogenesis and gliogenesis in the developing brain. In the midbrain, the distribution of TGF-α overlaps with tyrosine hydroxylase mRNA and fetal dopaminergic neurons. In culture, TCF-α enhanced survival and neurite outgrowth of neonatal rat dorsal ganglion neurons (EGF did not) and survival and differentiation of CNS neurons. TGF-α induced proliferation of neural precursor cells of the murine embryonic mesencephalon and further induced a significant increase in the number of astroglia and microglia in fetal rat medial septal cells. TGF-α increased glutamic acid decarboxylase activity and decreased choline actetyltransferase activity. Thus, TGF-α acted as a general neuronal survival factor affecting both cholinergic and GABAergic neurons. In addition, TGF-α is a mitogen for pluripotent brain stem cells. Forebrain subependyma contains nestin positive neural stem cells and their progeny, which are constitutively proliferating progenitor epithelial cells. A "knockout" mouse that was genetically engineered to delete the gene for TGF-α showed a reduction in neuronal progenitor cells in the subependyma and a reduction in neuronal progenitors that migrate to the olfactory bulb. In vitro, TGF-α promoted dopamine uptake in fetal rat dopaminergic neurons in a dose-dependent and time-dependent manner. TGF-α selectively promoted dopaminergic cell survival, enhanced neurite length, branch number and the soma area of tyrosine hydroxylase immunopositive cells. The levels of TGF-α were elevated in ventricular cerebrospinal fluid in juvenile parkinsonism and Parkinson's Disease and may represent a compensatory response to neurodegeneration. Further, TGF-α prevented a striatal neuronal degeneration in an animal model of Huntington's Disease. Accordingly, the administration to a subject or the contacting of neuronal precursor cells in vitro with a TGF-α polypeptide, fragment or mimetic of the invention is useful in promoting cell proliferation (including stem cell proliferation) and tissue repair in, for example, the central nervous system.

The fact that fetal brain tissue has been shown to have clear behavioral effects when transplanted into adult lesioned brains, has focused attention on human fetal tissue as a potential cell source in transplantation protocols designed to improve neurodegenerative disorders (Bjorklund, Nature 362:414–415, 1993; McKay, Trends Neurosci. 14:338–340, 1991). Nevertheless both ethical, as well as practical considerations make fetal tissue a difficult source to use. Expansion of neuronal stem cells whether fetal or otherwise using a TGF-α or polypeptide, fragment or mimetic of the invention provides an alternative source for obtaining the desired quantities of precursor cells for transplantation purposes. Fetal tissues or adult tissues containing precursors can be treated with a TGF-α polypeptide, fragment or mimetic of the invention as described earlier in order to expand the undifferentiated progenitor cell populations. Fetal cells can placed into primary culture using, for example, protocols developed by Sabate et al., Nature Gen. 9:256–260, 1995, before being treated with a TGF-α polypeptide, fragment or mimetic of the invention. By way of example but not limitation, the procedure is as follows: Primary cultures of human fetal brain cells can be isolated from human fetuses, obtained from legal abortions after 5 to 12 weeks of gestation. Expulsion can be done by syringe-driven gentle aspiration under echographic control. Fetuses collected in sterile hibernation medium are dissected in a sterile hood under a stereomicroscope. Brains are first removed in toto in hibernation medium containing penicillin G 500 U/ml, streptomycin 100 µg/ml, and fungizon 5 µg/ml. For fetuses of six to eight weeks of age the brain is separated into an anterior (telencephalic vesicles and diencephalon) and a posterior fraction (mesencephalon, pons and cerebellar enlage) and a posterior in toto after careful removal of meninges. For older fetuses, striatal hippocampal, cortical and cerebellar zones expected to contain proliferative precursor cells are visualized under the stereomicroscope and dissected separately. Cells are transferred to either Opti-MEM (Gibco BRL) containing 15% heat-inactivated fetal bovine serum (FBS) (Seromed), or to a defined serum-free medium (DS-FM) with human recombinant bFGF (10 ng/ml, Boehringer), which is a minor modification of the Bottenstein-Sato medium 39 with glucose, 6 g/l, glutamine 2 mM (Gibco BRL), insulin 25 µg/ml (Sigma) transferrin 100 µg/ml (Sigma), sodium selenite 30 nM (Gibco BRL), progesterone 20 nM (Sigma), putrescine 60 nM (Sigma), penicillin G (500 U/ml), streptomycin 100 µg/ml, and fungizon 5 µg/ml. Cells, approximately 40,000 per $cm^2$, are grown at 37° C. in an atmosphere containing 10% $CO_2$ in tissue culture dishes (Falcon or Nunc) coated with gelatin (0.25% wt/vol) followed by Matrigel (Gibco BRL, a basement membrane extract enriched in laminin and containing trace amounts of growth factors diluted one in 20). Cells in culture can be treated with a TGF-α polypeptide, fragment or mimetic of the invention in order to expand the population of the appropriate cells until the desired cell mass is reached for transplantation.

Any technique which provides for the isolation, propagation, and maintenance in vitro of hematopoietic stem cells (HSC) can be used in this embodiment of the invention. Techniques by which this can be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., J. Clin. Invest. 73:1377–1384, 1984). In a one embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., J. Cell Physiol. 91:335, 1977) or Witlock-Witte culture techniques (Witlock and Witte, Proc. Natl. Acad. Sci. USA 79:3608–3612, 1982).

Another technique for the isolation of USC is described by Milner et al, Blood 83.2057–2062, 1994. Bone marrow samples are obtained and are separated by Ficoll-Hypaque density gradient centrifugation, are washed, and stained using two-color indirect immunofluorescent antibody binding and then separated by fluorescence-activated cell sorting (FACS). The cells are labelled simultaneously with IgG antibodies such that $CD34^+$ hematopoietic stem cells, including the immature subset that lacks expression of individual lineage associated antigens, $CD34^+$ $lin^-$, are isolated from the cells collected from marrow.

Where hematopoietic progenitor cells are desired, the presence of hematopoietic progenitor cells and/or their progeny can be detected by commonly known in vitro colony forming assays (e.g., those that detect CFU-GM, BFU-E). As another example, assays for hematopoietic stem cells are also known in the art (e.g., spleen focus forming assays, assays that detect the ability to form progenitors after replating).

Epithelial stem cells (ESCs) or keratinocytes can be obtained from tissues such as the skin and the lining of the gut by known procedures (Rheinwald, Meth. Cell Bio. 21A:229, 1980). In stratified epithelial tissue such as the skin, renewal occurs by mitosis of precursor cells within the germinal layer, the layer closest to the basal lamina. Precursor cells within the lining of the gut provide for a rapid renewal rate of this tissue. ESCs or keratinocytes obtained from the skin or lining of the gut of a patient or donor can be grown in tissue culture (Rheinwald, Meth. Cell Bio. 21A:229, 1980; Pittelkow and Scott, Mayo Clinic Proc. 61:771, 1986). If the ESCs are provided by a donor, a method for suppression of host versus graft reactivity (e.g., irradiation, drug or antibody administration to promote moderate immunosuppression) can also be used.

Liver stem cells can be isolated by methods described in PCT Publication WO 94/08598, dated Apr. 28, 1994 and in U.S. Pat. No. 5,559,022 to Naughton et al. the disclosures of which are incorporated herein by reference.

Mammalian kidney emerges from the metanephric mesenchyme which induces the uteric bud to undergo a series of morphogenetic movements ultimately forming the mature urinary collecting system (Nigam and Brenner, Curr. Opin. Nephrol. Huper 1•J87–191, 1992. The uteric bud, an epithelial outgrowth of the Wolfian duct, contracts and induces condensing adjacent mesenchyme along differentiation pathways of epithelial divergence in early embryonic life. Attempts to study this process in vitro have been reported; metanephros in organ culture can be induced to form tubules using embryonic spinal cord as the inducer. While the specific transducing agents that lead to the induction of metanephric mesenchyme by the uteric bud in vivo or by spinal cord in vitro are not known, it is clear that differentiation program is induced in progenitor cells (Karp et al., Dev. Biol. 91:5286–5290, 1994).

After the precursors cells have been isolated according to the methods described above or other methods known in the art, the precursor cells can be contacted with an amount of a TGF-α polypeptide, a related polypeptide, fragment or mimetic of the invention effective to promote growth and proliferation under cell growth conditions (e.g., promoting mitosis) such that the cell proliferates to obtain an expanded precursor population according to the present invention.

In one embodiment, a TGF-α polypeptide, related polypeptide, fragment or mimetic of the invention can be used in conjunction with factors that inhibit differentiation such as Notch (see, U.S. Pat. No. 5,780,300). Under such conditions substantially no differentiation of the precursor cells would occur during expansion. The amount of differentiation that occurs can be assayed for by known assays, e.g., those that detect the presence of more differentiated cells by detecting functions associated with a particular stage of differentiation, e.g., expression of differentiation antigens on the cell surface or secretion of proteins associated with a particular state, or ability to generate various cell types, or detecting morphology associated with particular stages of differentiation.

Once the population has reached a desired titer, factors that allow at least some of the cells in the expanded population to differentiate can be added to the culture. Such factors can be added in order to achieve a desired differentiation state or to induce differentiation of the cells such that the cells express a desired phenotype. The cells can be differentiated to a terminally differentiated state if the function of that terminally differentiated cell is desired. Factors which promote differentiation are known in the art and include, for example, retinoic acid, dexamathosone, and dimethylsulfoxide (DMSO).

In one embodiment, the method uses a population of lymphoid stem cell progenitor cells, phenotypically characterized as $CD34^+$. The culture medium is a standard culture medium for stem cell cultures such as a 61.2 or 62.2 medium (Counter, EMBO J. 11:1921, 1992) or 80% Dulbecco's modified Eagle medium (such as high glucose with 1.0 μM GLN, 0.1 μM β mercaptoethanol and 1% nonessential amino acid stock, GIBCO-BRL) supplemented with human TGF-α polypeptide, fragment or a mimetic thereof at a concentration of from about 25 μg/ml to about 100 μg/ml. The cultures are grown up to a concentration of stem cells of about 0.5×1 cells/ml to about $5 \times 10^6$ cells/ml or more. The cells are then exposed to T cell differentiation factors (such as IL-2) for a period of about 2 days and then to an antigen for a period of about 2 to 3 days at an antigen concentration of from about 10 μg/ml to about 100 μg/ml. This two-stage procedure primes progenitor T cells and then mixes them with B cells. The source of the B cells can be isolated from peripheral blood (separated from T cells using standard purification procedures, such as glass wool columns of $CD4^+$ cells depleted with specific antibodies). The process "primes" the stem cells to differentiate into primed T cells. Typically, the antigen is a polypeptide or glycopeptide for an infectious disease, such as hepatitis C antigen or the gp120 protein of HIV. The cells are washed to remove antigen and the culture of predominantly primed T cells are administered back to the subject from which they were derived. In addition, primed B cells that provide a humoral (antibody) response to the antigen can also be administered.

The cells produced (e.g., expanded) by use of a TGF-α polypeptide, related polypeptide, fragment or mimetic of the invention can be made recombinant after expansion and used in gene therapy, protein production, or protein delivery techniques. In its broadest sense, gene therapy refers to therapy performed by the administration of a nucleic acid to a subject. The nucleic acid, either directly or indirectly via its encoded protein, mediates a therapeutic effect in the subject. By protein production means that a recombinant cell produced by use of a TGF-α polypeptide, fragment or mimetic of the invention can be recombinantly modified to produce a protein in vitro for collection, administration or modification. By protein deliver means that a recombinant cell modified to produce a polypeptide of interest is administered to a subject wherein the polypeptide of interest is expressed by the cell and secreted or otherwise delivered to the subject for a therapeutic or non-therapeutic purpose. Example of non-therapeutic purposes includes the expression of a detectable marker in vivo.

The present invention provides methods of gene therapy wherein a nucleic acid encoding a protein of therapeutic value (preferably to humans) is introduced into the precursor cells expanded according to the invention, before or after expansion, such that the nucleic acid is expressible by the precursor cells and/or their progeny, followed by administration of the recombinant cells to a subject.

The recombinant precursor cells of the present invention can be used in any of the methods for gene therapy available in the art. Thus, the nucleic acid introduced into the cells may encode any desired protein, e.g., a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see "The Development of Human Gene Therapy," Eds. Theodore Friedmann, Cold Springs Harbor Laboratory Press, Cold Spring Harbor, N.Y., 1999; Goldspiel et al., Clinical Pharmacy 12:488–505, 1993; Wu and Wu, Biotherapy 3:87–95, 1991; Tolstoshev, Ann. Rev. Pharmacol. Toxicol. 32:573–596, 1993; Mulligan, Science 260:926–932, 1993; and Morgan and Anderson, Ann. Rev. Biochem. 62:191–217, 1993; May, 1993, TIBTECH 11 (5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant precursor cells are used in gene therapy, a gene whose expression is desired in a patient or subject is introduced into the precursor cells such that it is expressible by the cells and/or their progeny, and the recombinant cells are then administered in vivo for therapeutic effect.

Precursor cells or expanded precursor cells can be used in any appropriate method of gene therapy, as would be recognized by those in the art upon considering this disclosure. The resulting action of a recombinant precursor cell or its progeny cells administered to a patient can, for example, lead to the activation or inhibition of a pre-selected gene in the patient, thus leading to improvement of the diseased condition afflicting the patient.

The desired gene is transferred to precursor cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those precursor cells are then delivered to a patient.

In this embodiment, the desired gene is introduced into a precursor cell prior to administration in vivo of the resulting recombinant cell. Such introduction can be carried out by any method known in the art, including but not limited to transfection, electroporation, microinjection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, Meth. Enzymol. 217:599–618, 1993; Cohen et al., Meth. Enzymol. 217:618–644, 1993; Cline, Pharmac. Ther. 29:69–92, 1985) and may be used in accordance with the present invention, provided that the necessary developmental and physiological functions of the recipient cells are not disrupted. The technique should provide for the stable transfer of the gene to the cell, so that the gene is expressible by the cell and preferably heritable and expressible by its cell progeny.

One common method of practicing gene therapy is by making use of retroviral vectors (see Miller et al., Meth. Enzymol. 217:581–599, 1993). A retroviral vector is a retrovirus that has been modified to incorporate a preselected gene in order to effect the expression of that gene. It has been found that many of the naturally occurring DNA sequences of retroviruses are dispensable in retroviral vectors. Only a small subset of the naturally occurring DNA sequences of retroviruses is necessary. In general, a retroviral vector must contain all of the cis-acting sequences necessary for the packaging and integration of the viral genome. These cis-acting sequences include: a) a long terminal repeat (LTR), or portions thereof, at each end of the vector; b) primer binding sites for negative and positive strand DNA synthesis; and c) a packaging signal, necessary for the incorporation of genomic RNA into virions. The gene to be used in gene therapy is cloned into the vector, which facilitates delivery of the gene into a precursor cell by infection or delivery of the vector into the cell.

Adenoviruses and HIV-1 based lentiviral vectors are also of use in gene therapy. Adenoviruses are especially attractive vehicles for delivering genes to respiratory precursor cells. Adenoviruses can also be used to deliver genes to precursor cells from the liver, the central nervous system, endothelium, and muscle. Adenoviruses have the advantage of being capable of infecting non-dividing cells. Kozarsky and Wilson, Current Opinion in Genetics and Development 3:499–503, 1993, present a review of adenovirus-based gene therapy. Other instances of the use of adenoviruses in gene therapy can be found in Rosenfeld et al., Science 252:431–434, 1991; Rosenfeld et al., Cell 68:143–155, 1992; and Mastrangeli et al., J. Clin. Invest. 91:225–234, 1993.

In a specific embodiment, the desired gene recombinantly expressed in the precursor cell to be introduced for purposes of gene therapy comprises an inducible promoter operably linked to the coding region, such that expression of the recombinant gene is controllable by controlling the presence or absence of the appropriate inducer of transcription.

In another embodiment, if a greater number of differentiated cells is desired before administering to a patient then the precursor cells can be differentiated prior to expansion. In another embodiment, one can expand and differentiate the precursor cells simultaneously such that greater numbers of differentiated cells are obtained.

The isolation of stem cells or precursor cells for use in the present invention can be carried out by any of numerous methods commonly known to those skilled in the art. For example, one common method for isolating stem cells or precursor cells is to collect a population of cells from a subject and use differential antibody binding, wherein cells of one or more certain differentiation stages are bound by antibodies to differentiation antigens, to separate the precursor or stem cells from the isolated population. Methods of separating the cells includes, for example, fluorescence activated cell sorting.

In one embodiment of the invention, epithelial stem cells or keratinocytes are obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a subject can be grown in tissue culture (Rheinwald, 1980, Meth. Cell Bio. 21A:229; Pittelkow and Scott, 1986, Mayo Clinic Proc. 61:771).

In another embodiment of the invention, mesenchymal progenitor cells are used in cell replacement therapy. Mesenchymal progenitor cells give rise to a very large number of distinct tissues, for example chondrocytes, osteoblasts, cartilage and bone (Caplan, J. Orth. Res. 641–650, 1991). Conditions have been defined under which chick mesenchymal cells differentiated into chondrocytes and bone. (Caplan, Exp. Cell. Res. 62:341–355, 1970; Caplan, 1981, 39th Annual Symposium of the Society for Developmental Biology, pp. 37–68; Caplan et al., Dilatation of the Uterine Cervix 79–98, 1980; DeLuca et al., J. Biol. Chem. 252:6600–6608, 1977; Osdoby et al., Dev. Biol. 73:84–102, 1979; Syftestad et al., Dev. Biol. 110:275–283, 1985). Mesenchymal cells capable of differentiating into bone and cartilage have also been isolated from marrow (Caplan, 1991, J. Orth. Res. 641–650). Caplan et al., 1993, U.S. Pat. No. 5,226,914 describes an exemplary method for isolating mesenchymal stem cells from bone marrow. Furthermore, the isolation of human marrow and the demonstration that cells deriving from it can sustain osteogenesis has been described, e.g., by Bab et al., Bone Mineral 4:373–386, 1988.

The mucosal epithelium of the intestine is in a continually dynamic state known as "epithelial renewal" in which undifferentiated stem cells from a proliferative crypt zone divide, differentiate and migrate to the luminal surface. Once terminally differentiated, mucosal epithelial cells are sloughed from the tips of the villi. The turnover of the crypt-villus cell population is rapid and occurs every 24–72 hours. Continuous exfoliation of the cells at the villus tip is counterbalanced by ongoing proliferation in the crypt so that net intestinal epithelial mass remains relatively constant. The rapidly-proliferating epithelium of the gastrointestinal tract is extremely sensitive to cytotoxic drugs that are widely used in cancer chemotherapy. By "gastrointestinal tract" is meant, for example, the tissues of the mouth, esophagus, stomach, small intestine, large intestine, rectum and anus. This "side effect" reduces the tolerated dose of such drugs as it can cause a breakdown of the GI barrier function and septic propagate a septic condition in a patient already immuno-compromised. This can also lead to life-threatening hemorrhage. Therefore, there is a need in the art for the development of products and delivery systems that stimulate the repair and rejuvenation of mucosal epithelium in the gastrointestinal tract to provide benefit to subjects having, for example, weight-loss disorders associated with chemotherapy and radiation therapy for cancer as well as disorders or diseases associated with pathogens such as HIV.

The replacement cells of the present invention can be transplanted into a patient for the treatment of disease or injury or for gene therapy by any method known in the art which is appropriate for the type of stem cells being transplanted and the transplant site. Hematopoietic stem cells can be transplanted intravenously, as can liver stem cells which will locate to the liver. Neural stem cells can be transplanted directly into the brain at the site of injury or disease.

The following describes exemplary methods which can be modified for the transplantation of replacement cells: Protocols for the isolation and transplantation of fetal tissues in humans have been reported and clinical trials involving these studies having been carried out. For example, Lindvall et al., Science 247:574–577, 1990, have described results regarding grafts and survival of fetal dopamine neurons after transplantation into brain. Rinsing and partial dissociation of precursor cells, if necessary, can be carried out by a modification of that described in Lindvall et al., Arch. Neurol. 46:615, 1989.

By way of example, implantation of cells into the brain can be performed as follows. Implantation is done at three sites in the left putamen with a stereotactic technique (Lindvall et al., Arch. Neurol. 46:615, 1989). For each site, 20 µl of the dissociated cells is drawn into the instrument (outer diameter, 1.0 mm). The cells are injected along a 10, 12 and 14 mm linear tract, respectively, in either 2.5 µl portions for 15 to 20 seconds each. Between each injection there is a 2 minute delay, and the cannula is then retracted 1 5 to 1.7 mm. After the final injection, the cannula is left in situ for 8 minutes before being slowly withdrawn from the brain. After surgery the cell viability is assessed following the procedure of Brundin et al., Brain. Res. 331:251, 1985.

Another example is outlined by Caplan et al., 1993, U.S. Pat. No. 5,226,914. Briefly, after marrow cells are harvested from bone marrow plugs and the marrow mesenchymal, stem cells are separated by centrifugation. The stem cells are isolated further by selective adherence to the plastic or glass surface of a tissue culture dish. The stem cells are allowed to proliferate, but not differentiate. Porous ceramic cubes composed of 60% hydroxyapatite and 40% β-tricalcium phosphate are added to the cells under a slight vacuum. The cubes with adhered cells are implanted into incisional pockets along the backs of nude mice. The mesenchymal stem cells differentiate into bone.

The titer of stem cells transplanted or the amount of a therapeutic which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

The precursor cells to be expanded in the present invention can be isolated from a variety of sources using methods known to one skilled in the art as described above, and can be of any animal, preferably mammalian, most preferably human, and can be of primary tissue, cell lines, etc.

The TGF-α polypeptides (e.g., SEQ ID NO:1), TGF-α fragments and mimetics thereof are particularly suited for delivery to a subject by means of a nucleic acid gene expression system ex vivo or in vivo. A variety of transfection techniques are currently available and used to transfer DNA in vitro into cells; including calcium phosphate-DNA precipitation, DEAE-Dextran transfection, electroporation, liposome mediated DNA transfer or transduction with recombinant viral vectors. Such ex vivo treatment protocols have been used to transfer DNA into a variety of different cell types including epithelial cells (U.S. Pat. No. 4,868,116; Morgan and Mulligan WO87/00201; Morgan et al., Science 237:1476–1479, 1987; Morgan and Mulligan, U.S. Pat. No. 4,980,286), endothelial cells (WO89/05345), hepatocytes (WO89/07136; Wolff et al., Proc. Natl. Acad. Sci. USA 84:3344–3348, 1987; Ledley et al., Proc. Natl. Acad. Sci. 84:5335–5339, 1987; Wilson and Mulligan, WO89/07136; Wilson et al., *Proc. Natl. Acad. Sci.* 87:8437–8441, 1990) fibroblasts (Palmer et al., Proc. Natl. Acad. Sci. USA 84:1055–1059, 1987; Anson et al., Mol. Biol. Med. 4:11–20, 1987; Rosenberg et al., Science 242:1575–1578, 1988; Naughton & Naughton, U.S. Pat. No. 4,963,489), lymphocytes (Anderson et al., U.S. Pat. No. 5,399,346; Blaese, R. M. et al., Science 270:475–480, 1995) and hematopoietic stem cells (Lim, B. et al. Proc. Natl. Acad. Sci. USA 86:8892–8896, 1989; Anderson et al., U.S. Pat. No. 5,399, 346). A summary of typical protocols, methodology, and vectors is provided in "The Development of Human Gene Therapy," Ed. Theodore Friedmann, Cold Spring Harbor Laboratory Press, New York, 1999, the disclosure of which is incorporated herein.

Direct in vivo gene transfer has recently been attempted with formulations of DNA trapped in liposomes (Ledley et al., J. Pediatrics 110:1, 1987); or in proteoliposomes that contain viral envelope receptor proteins (Nicolau et al., Proc. Natl. Acad. Sci. U.S.A. 80:1068, 1983); and DNA coupled to a polylysine-glycoprotein carrier complex. In addition, "gene guns" have been used for gene delivery into cells (Australian Patent No. 9068389). Naked DNA, or DNA associated with liposomes, can be formulated in liquid carrier solutions for injection into interstitial spaces for transfer of DNA into cells (Felgner, WO90/11092).

As described above, polynucleotide sequences encoding a TGF-α polypeptide or function peptide fragment or mimetic, can be cloned into vectors suitable for delivery to host cells for expression. In particular retroviral vectors containing the polypeptides of the invention are particularly suitable for delivering polynucleotides to cells for gene therapy. Current strategies for gene therapy are reviewed in "The Development of Human Gene Therapy," Ed. Theodore Friedmann, Cold Spring Harbor Laboratory Press, New York, 1999, the disclosure of which is incorporated herein.

Delivery of a polynucleotide of interest may be accomplished in vivo by administration of the vectors to an individual subject, typically by systemic administration (e.g., intravenous, intraperitoneal, intramuscular, subdermal, or intracranial infusion). Alternatively, the vectors may be used to deliver polynucleotides to cells ex vivo such as cells explanted from an individual patient (e.g., tumor-infiltrating lymphocytes, bone marrow aspirates, tissue biopsy) or universal donor hematopoietic stem cells, followed by reimplantation of the cells into a patient, usually after selection for cells which have incorporated the polynucleotide.

The vectors may be used for gene therapy to reduce the incidence of weight-loss and associated disorders resulting from particular diseases (e.g., cancer), or viral diseases (e.g., AIDS, mononucleosis, herpesvirus infection, cytomegalovirus infection, papillomavirus infection) or to modify the genome of selected types of cells of a patient for any therapeutic benefit.

The vectors of the invention can be used to introduce polynucleotides into a variety of cells and tissues including myeloid cells, bone marrow cells, lymphocytes, hepatocytes, fibroblasts, lung cells, epithelial cells and muscle cells. For example, polynucleotides encoding a TGF-α polypeptide may be transferred to stem cells.

Mast cell degranulation often is a precursor to acute gastrointestinal injury and to an inflammatory response. The mediators released from mast cells often represent an early event in many disease indications associated with inflammation. Compounds that have activity to degranulate mast cells (such as stem cell factor (SCF), reserpine and polymixin B), induce gastrointestinal mucosal injury and result in severe hemorrhage and tissue necrosis. In addition, administration of mast cell stabilizers, such as sodium cromoglycate, inhibited gastric mucosal injury induced by ethanol and aspirin. (Kalia and Bandhan, J. Gastroenterolgy Hep., 13:1081–1083, 1998) Repeated degranulation of mast cells induces gastric mucosal injury by a mechanism dependent on nitric oxide (NO) generation. Selective inhibition of the inducible NO synthesis (NOS) by compounds, such as dexamelhasone and aminoguanidine, suggested the NOS:NO system as the target mechanism. Mast cell mediators include pro-inflammatory cytokines or agents such as histamine, serotonin, prostanoids, platelet activating factor, leukotrienes B and C, and pro-inflammatory cytokines IL-1, IL-6 and TNFα.

TGF-α polypeptide, fragments, and mimetic provide mast cell protection from degranulation in cisplatinum-treated mice. Therefore, in view of the relationship between mast cell degranulation and mucosal toxicity, a TGF-α polypeptide, fragments, and mimetic reduce mast cell degranulation and thus prevent mucosal toxicity after exposure to agents that degranulate mast cells and the pro-inflammatory cytokines causing an inflammatory reaction in reaction to mast cell products. Such mast cell products include the cytokines IL-1, IL-6 and TNFα. Accordingly, in view of the effects of a TGF-α polypeptide, fragments, and mimetic on mast cells, such therapeutic agents have a generalized anti-inflammatory activity.

The present invention further provides a method for protection of tissue or organs damaged or likely to be damaged by a cytotoxic agent (including radiation), wherein the organ or tissue is selected from the group consisting of kidney, intestine, pancreas, brain and lung, comprising administering an effective amount of a TGF-α polypeptide, fragments, and mimetic to the damaged tissue.

The invention also provides methods of modulating weight-loss associated with disease and disorders of the gastrointestinal tract, for example, those associated with viral infections and chemotherapy by administering TGF-α or related polypeptides or fragments thereof which retain TGF-α biological activity (e.g., SEQ ID NO:1, 2, or 3, and the peptides of formula I, II, or III).

The invention further provides a pharmaceutical composition comprising a peptide in a pharmaceutically acceptable carrier, wherein the peptide compound comprises at least about a 10 to 18-membered peptide compound of formula I (SEQ ID NO:4, including members of SEQ ID NO:5 attached to SEQ ID NO:4 and including SEQ ID NO:6). Preferably, at least one or more of the seven amino acids of formula II are added to the C terminus Cys moiety. Most preferably, the functional peptide is 18 amino acids in length wherein $X_{1a}$ is Val, $X_{1b}$ is Gly, $X_{1c}$ is Ala and $X_4$ is Gly. The peptides described herein are all useful in the methods of the invention.

The invention further provides a bifunctional compound that acts as a TGFα mimetic, comprising a compound of formula III:

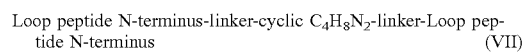

Loop peptide N-terminus-linker-cyclic $C_4H_8N_2$-linker-Loop peptide N-terminus (VII)

wherein the linker moiety is designed to link the N-terminus of the Loop peptide to a nitrogen atom of the ring $C_4H_8N_2$ and wherein the "loop peptide" comprises at least an 11-membered peptide compound of formula II:

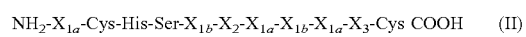

$NH_2$-$X_{1a}$-Cys-His-Ser-$X_{1b}$-$X_2$-$X_{1a}$-$X_{1b}$-$X_{1a}$-$X_3$-Cys COOH  (II)

wherein $X_{1a}$ and $X_{1b}$ are independently Val, Gly or Ala; $X_2$ is Tyr or Phe; $X_3$ is Arg or Lys; and the two Cys moieties are linked via a disulfide bond to form an at least 11-amino acid functional peptide having TGF-α activity. Preferably, at least one or more of the following amino acids are added to the C terminus Cys moiety from formula III:

-$X_4$-His-$X_{1c}$-$X_4$-$X_5$-$X_6$-$X_{1c}$  (III)

wherein $X_4$ is Glu or Asp, wherein $X_5$ is Leu or Ile, and wherein $X_6$ is Asp or Glu. Preferably, $X_{1a}$ is Val, $X_{1b}$ is Gly and $X_{1c}$ is Ala. Preferably, the linker group is independently selected from the group consisting of substituted or unsubstituted $C_{1-6}$ alkyl, substituted or unsubstituted $C_{2-6}$ alkenyl, substituted or unsubstituted $C_{1-6}$ alkoxy, xylenyl, wherein the substitutions are selected from the group consisting of oxo, epoxyl, hydroxyl, chloryl, bromyl, fluoryl, and amino. Preferably, $X_2$ is Tyr, and $X_3$ is Arg. Most preferably, the functional peptide is 18 amino acids in length wherein $X_{1a}$ is Val, $X_{1b}$ is Gly, $X_{1c}$ is Ala and $X_4$ is Gly.

The invention will now be described in greater detail by reference to the following non-limiting examples.

EXAMPLE 1

Figure 2:
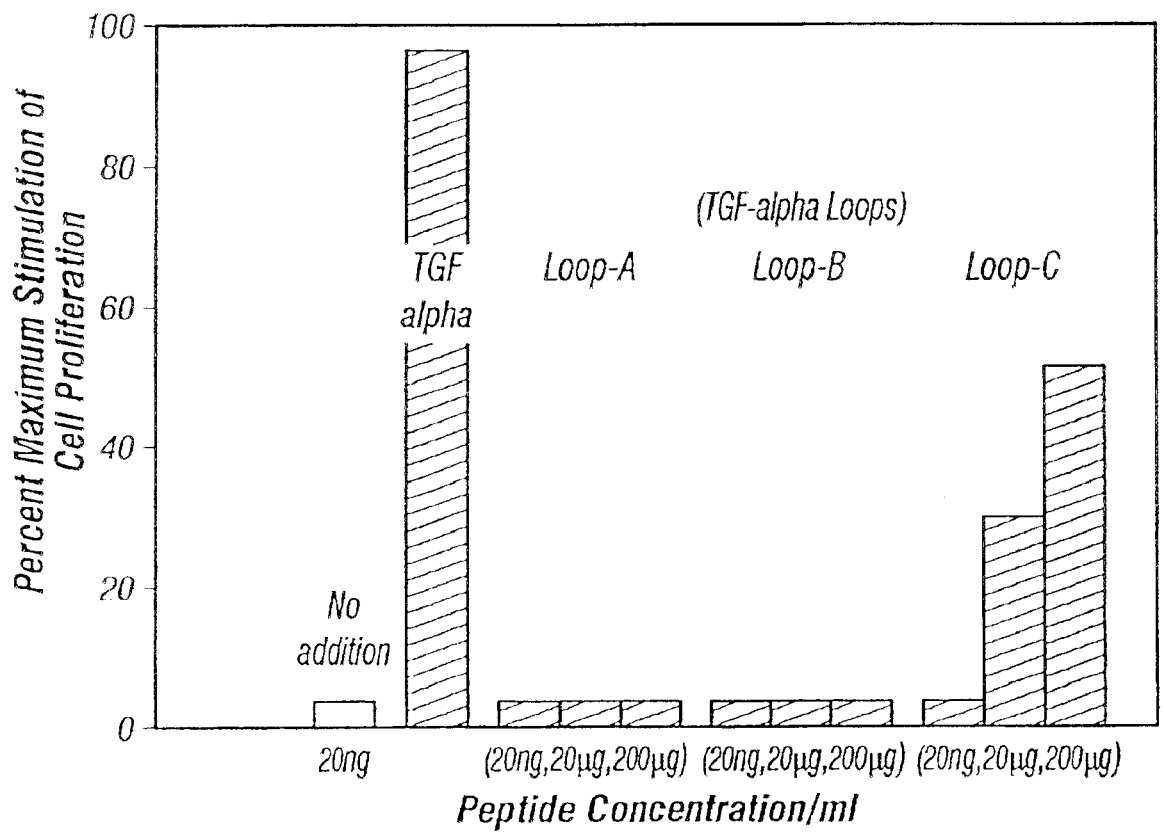
FIG. 2 shows a graph comparing TGF-α biological activity of the three loop peptide regions of TGFα (see FIG. 1) wherein Loop A is amino acids 1–21 (starting at the N terminus), Loop B is amino acids 16 to 32 and Loop C is amino acids 33 to 50. Only Loop C showed significant TGF-α activity as determined by cell proliferation and in a dose response fashion.

Each of the three loop regions in human TGFα was investigated for TGFα-like biological activity, such as stimulation of cellular proliferation as measured by $^3$H thymidine incorporation of stem cells. As shown in FIG. 2, only the Loop C peptide (corresponding to amino acids 33–50) showed significant TGF-α biological activity as compared to data obtained with TGF-α 50 amino acid polypeptide or even the altered splice 57 amino acid polypeptide and is therefore a TGF-α mimetic peptide. Accordingly, data from TGFα or TGF-α57 show what can be called "TGF-α activity" and that these are predictive of activity of the functional TGF-α peptide and similar functional TGF-α peptides embodied in the genus of formula I with or without the addition of a "tail" region of formula II. These data predict activity for the functional TGF-α peptides when activity is also shown for TCF-α or for TGF-α57.

EXAMPLE 2

Hematopoiesis

Figure 3:
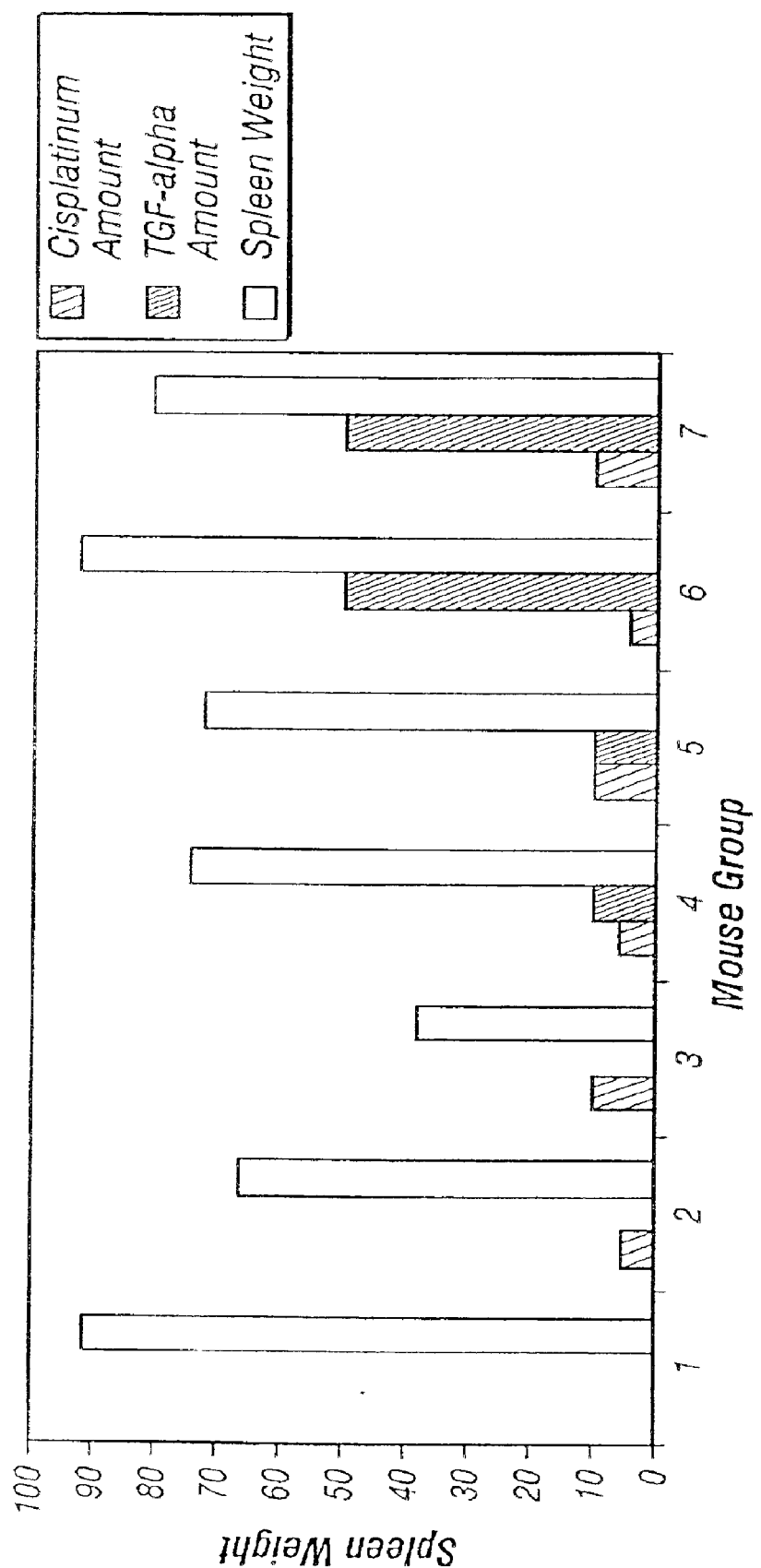
FIG. 3 shows a graph of mouse spleen weights that were treated with Cis Platinum (CP) at either 5 mg/kg or 10 mg/kg and with TGF-α at concentrations of 10 µg/kg or 50 µg/kg. These data show that TGFα treatment caused a return to normal spleen weights despite CP treatment that reduced spleen weights significantly.

TGF-α and related polypeptides, such as TGF-α57, showed surprising enhancing activity in an in vivo model of general hematopoiesis when administered in conjunction with a potent cytotoxic agent Cis Platinum (CP). FIG. 3 shows a graph of mouse spleen weights that were treated with CP at either 5 mg/kg or 10 mg/kg and with TGF-α57 at concentrations of 10 μg/kg or 50 μg/kg. These data show that TGF-α57 treatment caused a return to normal spleen weights despite CP treatment that reduced spleen weights significantly. This in vivo experiment is a predictive model for hematopoiesis in humans as CP is a cytotoxic agent commonly used for cancer chemotherapy that is known to significantly reduce trilineage hematopoietic cells. Hematopoietic and myeloid cells are red blood cell precursors, platelet precursors (megakaryocytes), and immune (white) blood cell precursors of various forms of T cells, B cells and macrophages. Moreover, platelet counts were higher in those mice injected with TGF-α57 (and CP) as opposed to CP alone were such counts were significantly reduced from normal. It should be noted that references to TGF-α as a human 50 amino acid polypeptide further include reference to human TGFα57 as an alternative variant.

The experiment procedure dosed those animals to be treated with TGFα 57 4 hours prior to challenge with CP. A single dose of CP was administered. Additional doses (as indicated) of TGFα 57 were made at 24 hours, 48 hours, 72 hours and 96 hours after the CP dose. All doses were made by IP injection. Controls were dosed with saline instead of either or both of CP and TGF-α57.

The animals were sacrificed about 4 hours after the last TGF-α57 (or saline) dose. Key organs were removed and spleens were immediately weighed after a clean incision. All the relevant organs were placed in formalin, transported for bistopathological analysis, mounted, sectioned, stained and observed. The results of this histological analysis of the spleens for hematopoietic effect and the GI tract (below) provided surprising and unexpected data of the effect of TGF-α57 activity.

H&E-stained spleens of a CP-treated mouse spleen (10 mg/kg) showed apoptotic cells (densely stained with fragments of nuclei) in the germinal center (GC). T cells in the central arterial area showed the absence of a marginal zone and much fewer erythrocytes and T cells in the perifolecular area. A normal mouse spleen (no CP and no TGF-α57) fixed in formalin showed an arteriole enriched for T cell progenitors. There was erythrocytes in the perifollicular zone surrounding both the T cell and B cell compartments of white pulp. A mouse spleen treated with CP (10 mg/kg) and TGF-α57 (50 μg/kg) showed an increased number of T cells and erythrocytes in the perifollicular zone. The T cells stained for the T-cell receptor but were negative for CD4 and CD8 markers. Accordingly, the T-cells are double null T-cell progenitors induced by TGF-α administration.

These in vivo data in a predictive model of hematopoiesis and confirmed by blinded histological analysis (the histologist/pathologist was blinded as to the treatment history of the coded tissues received) providing surprising evidence of the utility of peptides having TGF-α activity to augment hematopoiesis and genesis of immune cells following cytotoxic exposure. These data predict and provide a reasonable correlation that TGF-α and the peptides of formula I, formula II and formula III are useful therapeutic agents for enhancing hematopoiesis following or during cytotoxic therapy, such as cancer treatment. Therefore, a useful method for improving cancer chemotherapy is to combine either TGF-α or a peptide from formula I, II, III, IV, V, or VI or combinations thereof with cytotoxic treatment regimens to reduce dose-limiting side effects of cytotoxic agents.

An additional experiment investigated TGF-α activity (using TGF-α57) on human bone-marrow enriched CD34 cells. FACS-sorted human CD34 positive and CD38 negative cells were cultured in liquid primary cultures in Iscove's modified Dulbecco's media with supplements. TGFα (57) was added alone (10 ng/ml) and exhibited a 35% increase in CD34 positive progenitor cells. Stem Cell Factor (SCF) was used as a positive control (500 ng/ml) and provided a three-fold increase in CD34 positive cells. When a combination of SCF (500 ng/ml) and TGFα (10 ng/ml) was added, a synergistic 12-fold increase in CD34 positive cells was observed. An unexpected result was the stimulation of the proliferation of dendritic precursor cells in the TGF-α treated cultures.

EXAMPLE 3

Mucositis and Gastrointestinal Diseases

The small intestine comprises the duodenum, jejunum and ileum. It is the principal site for absorption of digestive products from the GI tract. Digestion begins in the stomach and is completed in the small intestine in association with the absorptive process. The intestinal mucosa surface is made up of numerous finger-like projections called villi. In addition, mucosal epithelium between the basis of the villi is formed into the crypts which contain stem cells.

TGFα or a peptide from formula I, formula II, formula III, formula IV, formula V, or formula VI having TGFα activity or combinations thereof are also useful for treating mucositis associated intestinal bleeding, dyspepsia caused by with cytotoxic therapy and for improving the barrier function of the GI tract compromised by cytotoxic therapy. The in vivo experiment with seven groups of mice described above for hematopoietic effects noted in spleens also examined the GI tract of these treated mice. Histological examination of mouse intestines showed the following: CP (single ip dose of 10 mg/kg) treated intestine, when cross-sectioned, showed significant injury to the villi. Specifically, the villi are necrotic, the crypts are in irregular shapes, and the tips of the crypts were exhibiting loss of cellular integrity. A cross section of a normal mouse GI tract (no CP and no TGFα57) showed a normal intestinal surface with villi having long and slender mucosal projections with a core of lamina propria covered by a luminal epithelial layer. A single row of intestinal crypt is found at the base of the mucosa. These crypts that lie between adjacent villi are surrounded by the same lamina propria that form the villous cores. Both columnar absorptive cells and goblet cells cover the villous surfaces. The goblet cells contain apical clear vacuoles. A cross section of a mouse intestine exposed to both the CP (10 mg/kg) and TGFα57 (50 µg/kg) showed that the intestinal structure was very similar to the normal intestinal structure. Specifically, the villus was long and slender. Both absorptive cells and goblet cells were visible at the surface of the villi, and there was an abundant amount of goblet cells on the surface.

A 160× magnification of the intestines of a CP-treated mouse, a normal mouse and a Aim CP treated and TGFα57 treated mouse at the same doses as described above. The CP-treated mouse showed injured villi with degenerating and necrotic tips. Red blood cells were observed in the damaged villi. The crypts were irregularly shaped and in had various heights. The normal mouse showed smooth villi tips of the villi and nuclei of enterocytes were observed throughout the villus. The crypts were similar in height and had a regular shape. The CP treated and TGF-α treated mouse had normal appearing villi as described for the normal mouse. The crypts also appeared normal.

Further CP (10 mg/kg) treated without TGF-α57 mice and CP (10 mg/kg) and 50 µg/kg of TGF-α57 treated mice intestines when examined under higher magnification showed severely injured crypt surfaces in the CP treated mice due to cell death and necrosis. Red cells were visible at the damaged surface indicating intestinal bleeding. In addition, the CP-treated mouse showed a loss of brush borders and very little of a glycocalyx or fuzzy coat. Globlet cells appeared interspersed, necrotic and fewer in number than normal. The effect of TGF-α treatment showed protection of the villa surface. Specifically, the epithelial cells appeared normal with extended brush borders The nuclei were very densely stained and elongated.

Figure 4:
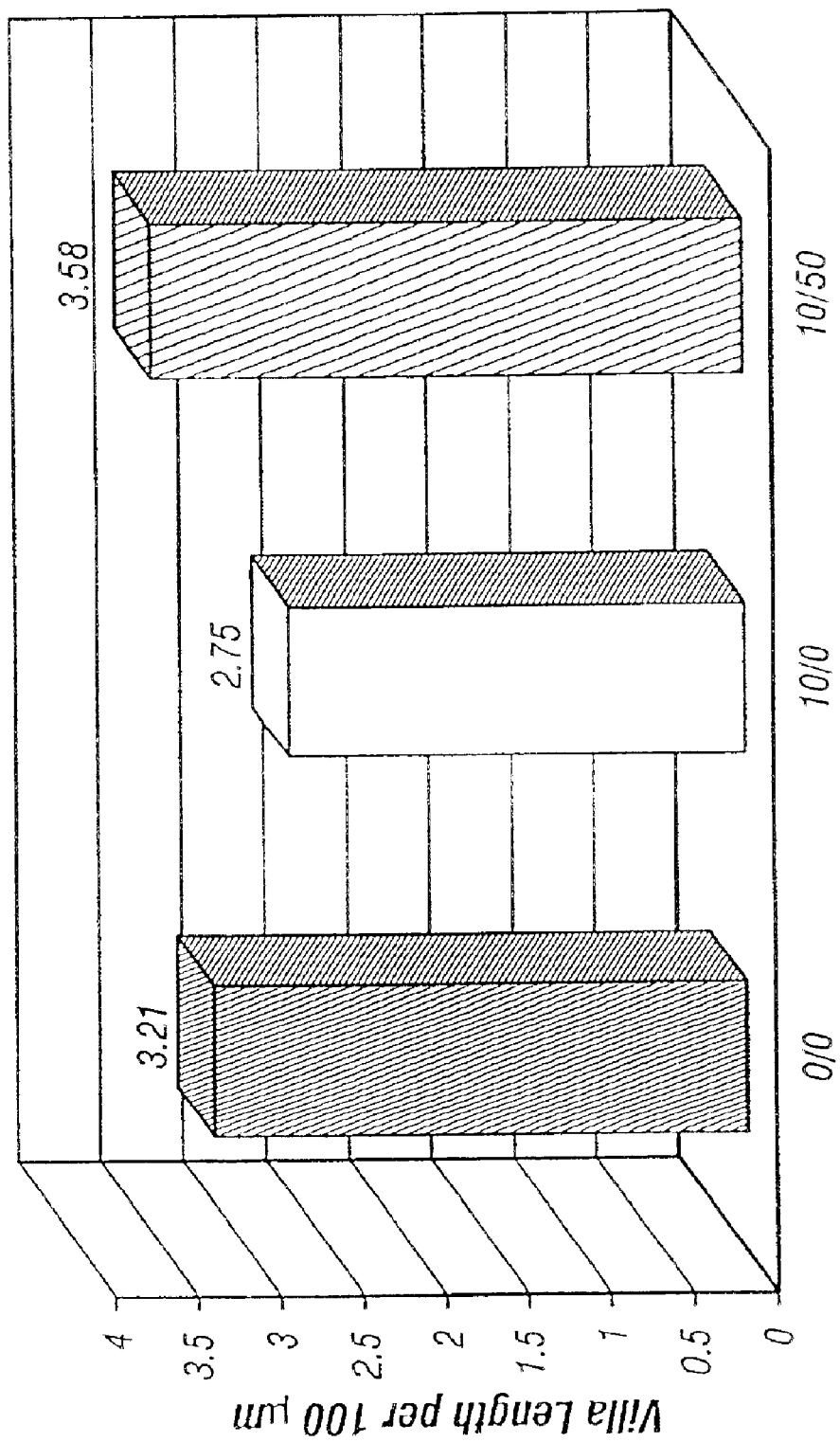
FIG. 4 depicts a summary of histological data that measured average crypt height of the three groups of mice. TGF-α57 treatment (50 µg/kg) was able to more-than-restore crypt height loss from CP treatment.

The histological data is summarized in FIG. 4 that measured average crypt height of the three groups of mice. TGFα57 and TGF-α (50 a.a.) treatment (50 µg/kg) was able to more-than-restore crypt height loss from CP treatment.

An alcian blue staining method permitted differentiation of absorptive cells and goblet cells. Goblet cell mucus is stained a blue color while the absorptive cells remain less stained. Stains of intestine from normal mice, CP only treated (10 mg/kg) and both CP (10 mg/kg) and TGFα57 (50 µg/kg) treated mice showed significant differences. In the normal intestine each villus extended from the luminal surface to the basal muscularis mucosal surface. Goblet cells were scattered and predominated in the base of the villus whereas columnar absorptive cells lined the luminal surface. In the CP treated mouse, the alcian blue staining showed villi that contained fewer number of goblet cells (than normal). The injured absorptive and goblet cells were degenerating at the tip of the villi and abundant secretory mucus material was stained in the luminal surface. In the CP/TGF-α mouse, there were an increased number of goblet cells scattered throughout the villi. The intestinal villi appeared normal with elongation. The majority of enterocytes did not appear to be alcian blue stained positive. The luminal plasma membranes of the villi were well protected by TGF-α treatment. The number of goblet cells was counted on the average unit length of intestine. TGFα treatment not only increased the number of goblet cells but also increased the number from CP treatment to a higher level than normal intestine.

Accordingly, these data show the effects of TGFα, and the functional peptides having TGF-α activity from formula I, formula II, formula III, and formula IV having therapeutic activity to treat or prevent mucositis associated with cytotoxic drug therapy and for inflammatory bowel diseases. Moreover, the histological effect showing that there was a prevention of mast cell degranulation, provides additional data supporting the gastrointestinal applications for TGFα, and the functional peptides having TGF-α activity of formula I, formula II, formula III, and formula IV.

EXAMPLE 4

Immune Related Diseases

In addition, TGF-α activity resulted in stimulation of proliferation of select immune cells (particularly of the T cell lineage) after administration to mice after immune-suppression of CP administration. The stimulated immune cells were phenotypically identified as CD4 positive T cells and double null CD4 negative CD8 negative T cell progenitors. Thus, TCF-α activity (e.g., from TGFα57 administration) resulted in generation of T-cells with characteristics that regulated immune functions. Therefore, these data predict that TGFα activity and the functional peptides of formula I, formula II, formula III, and formula IV will be effective in treating autoimmune diseases by mitigating over-inflammatory reactions. The in viva activity of TGFα (and the functional peptides of formula I, formula II, formula III, and formula IV) to stimulate early T cell progenitors in the release of TH-1 and TH-2 cytokines and this regulation of immune phenomena. The stimulation of select immune cells, in particular cells of a T cell lineage, was seen consistently in the mice who received CP and TCF-α57 in lymphoid tissue, Peyers Patches and the spleen. Further, recruitment of help via CD4 cells in some cases boosts immune system function in general.

TGF-α administration prevented mast cell degranulation and subsequent histamine release. In addition TGF-α has effects in downregulating TNF-α receptors in vivo and downregulating IL-6 and MIP in viva, including blocking neutrophil trafficking. This is a parallel activity that is in addition to the gastrointestinal anti-inflammatory activity and prevention of mucositis of TGFα (and the functional peptides of formula I, formula II, formula III, and formula IV) described herein.

EXAMPLE 5

In order to determine the effects of TGF-α polypeptides on weight-loss four groups of rats were tested. The experiment was designed to compare two of the peptides of TGF-α (SEQ ID NO:1 and SEQ ID NO:3) on weight-loss in the presence of a chemotherapeutic drug, cisplatin.

All animals were dosed over a period of 5 days. Group 1 animals received cisplatin at 10 mg/kg, Group 2 animals received cisplatin at 10 mg/kg plus TGF-α (SEQ ID NO: 1) at 50 µg/kg; Group 3 animals received cisplatin at 10 mg/kg plus TGF-α57 (SEQ ID NO:3) at 50 µg/kg, and Group 4 animals received TGF-α (SEQ ID NO:1) at 50 µg/kg. Following completion of the dosing protocols animals from each group were measure and organs/tissues were harvested and placed in buffered formalin. The tissues measured included lungs, spleens, kidneys, pancreas, intestines and tongues.

Figure 5:
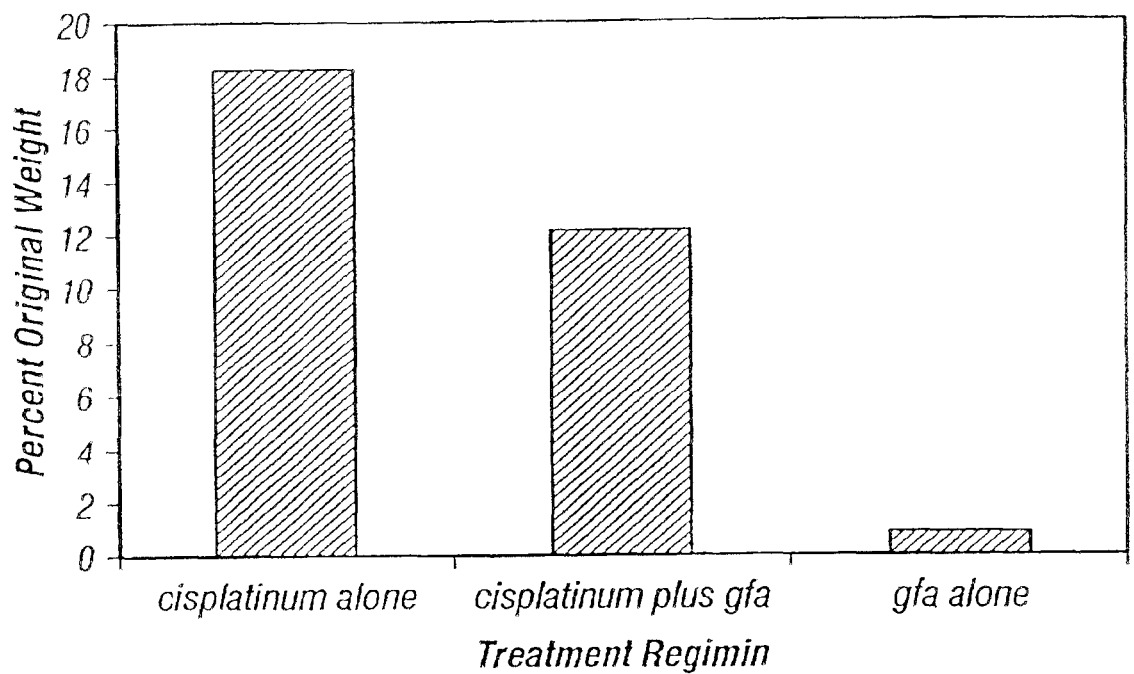
FIG. 5 shows a graph depicting the effects of cisplatinum-alone, cisplatinum and a TGF-α polypeptide, and a TGF-α alone on weight loss of mice.
Figure 6:
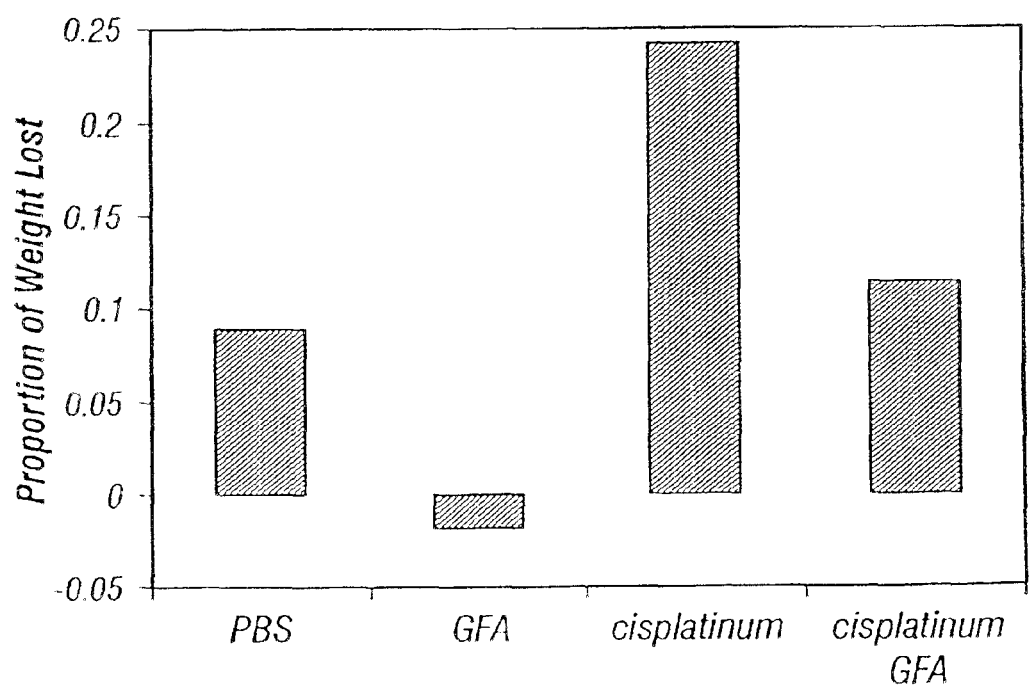
FIG. 6 shows weight loss in mice following cisplatin administration with and without concurrent TGF-α treatment. The graph shows (from left to right) the proportion of weight-loss in the presence of PBS alone, TGF-α alone, cisplatin alone, and cisplatin+TGF-α.

In the 9 animals in group 1 (cisplatin treatment), the average weight loss was 18.3%; in the 13 animals in groups 2 and 3 (cisplatin+TGF) the average weight loss was 12.1%; and in the 6 animals in group 4 (TGF alone) the average weight loss was 0.9% (FIG. 5).

In addition, studies of TGF-α for the treatment of diarrhea in non-human primates was also performed. A 6-year old non-human primate exhibiting chronic inflammatory-like gastrointestinal symptoms was treated with TGF-α at 300 µg/kg intraperitoneally once and subsequently 50 µg/kg S.C. for 6 days. The primate showed a steady increase in stool consistency and the monkey showed steady weight gain through the treatment period (see Table 1 and 2). This weight gain was maintained at least for several weeks post treatment. In addition, the reduction of SEGs (see column 6, Table 1) neutrophils correlates with reduction in inflammation associated with neutrophil influx and concomitant pro-inflammatory cytokines. No adverse effects were noted in hematology or serum chemistries, or in the primates attitude, behavior or appetite.

TABLE 1

| Time | wt. | hemoglobin | pcv % | wbc | Seg | Bands | Lymph | Monos | Eos | Basos | Abn. Cells | Platelets | CD4+ | CD8+ | Dual CD8+ CD4+ |
|---|---|---|---|---|---|---|---|---|---|---|---|---|---|---|---|
| 1 | 5.80 | 12.6 | 40.3 | 16.6 | 76% | 0% | 19% | 5% | 0% | 0% | 0% | 543 | 28.4% | 56.3% | 6.7% |
| 2 | 6.33 | 11.1 | 38.0 | 20.2 | 69% | 0% | 20% | 10% | 1% | 0% | 0% | 567 | | | |
| 3 | 6.74 | 9.2 | 32.1 | 10.3 | 61% | 0% | 34% | 4% | 1% | 0% | 0% | 456 | 36.7% | 53.1% | 6.3% |
| 4 | 8.21 | 10.3 | 34.2 | 8.4 | 48% | 0% | 42% | 9% | 1% | 0% | 0% | 534 | 31.3% | 54.0% | 9.1% |
| 5 | 8.93 | 10.8 | 37.1 | 11.2 | 46% | 0% | 45% | 8% | 0% | 1% | 0% | 425 | 33.4% | 49.8% | 8.1% |
| 6 | 9.42 | 11.5 | 38.1 | 15.5 | 56% | 1% | 31% | 11% | 1% | 0% | 0% | 434 | 35.1% | 50.3% | 7.7% |

TABLE 2

| Time | Na+ | K+ | Cl− | Glu | BUN | Creatine | Total Protein | Albumin | Albumin corrected | Total Billirubin | Ca2+ | Alk Phos | ALT (GPT) | AST (GOT) | GGT |
|---|---|---|---|---|---|---|---|---|---|---|---|---|---|---|---|
| 1 | 133 | 3.3 | 87 | 73 | 45 | 0.6 | 8.6 | 4.9 | 5.9 | 1.2 | 11.6 | 103 | 8 | 26 | 57 |
| 2 | 144 | 4.8 | 95 | 51 | 19 | 0.5 | 7.4 | 3.7 | 4.4 | | | | | | |
| 3 | 146 | 4.6 | 107 | 68 | 16 | 0.5 | 7.2 | 2.9 | 3.5 | 0.3 | 9.8 | 116 | 17 | 45 | 89 |
| 4 | 150 | 4.4 | 107 | 50 | 19 | 0.7 | 7.1 | 2.9 | 3.5 | 0.3 | 9.7 | 130 | 25 | 34 | 91 |
| 5 | 148 | 4.0 | 108 | 25 | 18 | 0.6 | 6.6 | 2.5 | 3.0 | 0.2 | 9.1 | 107 | 19 | 37 | 64 |
| 6 | 145 | 3.8 | 108 | 21 | 22 | 0.5 | 7.0 | 2.5 | 3.0 | 0.3 | 9.3 | 113 | 15 | 34 | 58 |

Note: Blood glucose levels are generally well below the normal reference range. This is not an abnormality. Albumin results require a correction factor for non-human primates, which is calculated into the second "Albumin corrected" column.

Note Blood glucose levels are generally well below the normal reference range. This is not an abnormality. Albumin results require a correction factor for non-human primates, which is calculated into the second "albumin corrected" column.

While the invention has been described in detail with reference to certain preferred embodiments thereof, it will be understood that modifications and variations are within the spirit and scope of that which is described and claimed.

What is claimed is:

1. A method for inducing the activity of CD34 positive progenitor cells of a subject in vivo in need of such treatment, comprising:
   contacting a tissue with a TGF-α57 polypeptide (SEQ ID NO:3), in an amount effective to induce cell proliferation, migration, or differentiation, thereby inducing the activity of CD34 positive progenitor cells of a subject in vivo in need of such treatment.

2. The method of claim 1, wherein the contacting is by continuous infusion of the a TGF-α57 polypeptide (SEQ ID NO:3).

3. The method of claim 1, wherein the contacting is by bolus or single administration of the TGF-α57 polypeptide (SEQ ID NO:3).

4. The method of claim 1, wherein the tissue is a musculoskeletal tissue, a gastrointestinal tissue, or a urogenital tissue.

5. The method of claim 1, wherein the tissue is selected from the group consisting of a musculoskeletal tissue, a gastrointestinal tissue, a urogenital tissue, and a neurological tissue.

6. The method of claim 1, wherein the need of such treatment results from cytotoxic or immune-suppressing therapy.

7. The method of claim 1, wherein the need of such treatment results from ARC or AIDS.

8. The method of claim 1, wherein the subject is a mammal.

9. The method of claim 8, wherein the mammal is a human.

10. The method of claim 1, wherein the contacting is at the site of the tissue.

* * * * *